US005484602A

United States Patent [19]

Stanley et al.

[11] Patent Number: 5,484,602
[45] Date of Patent: Jan. 16, 1996

[54] METHODS AND COMPOSITIONS FOR NONINVASIVE DOSE-TO-EFFECT ADMINISTRATION OF DRUGS WITH CARDIOVASCULAR OR RENAL VASCULAR ACTIVITIES

[75] Inventors: Theodore H. Stanley, Salt Lake City; Brian Hague, West Valley City, both of Utah

[73] Assignee: University of Utah Research Foundation, Salt Lake City, Utah

[21] Appl. No.: 376,642

[22] Filed: Jan. 20, 1995

Related U.S. Application Data

[63] Continuation of Ser. No. 209,113, Mar. 9, 1994, abandoned, which is a continuation of Ser. No. 90,485, Jul. 12, 1993, abandoned, which is a continuation of Ser. No. 732,723, Jul. 18, 1991, abandoned, which is a continuation of Ser. No. 421,068, Oct. 13, 1989, abandoned, which is a division of Ser. No. 60,046, Jun. 8, 1987, Pat. No. 4,885,173, which is a continuation-in-part of Ser. No. 729,301, May 1, 1985, Pat. No. 4,671,953.

[51] Int. Cl.$^6$ ............................................. A61K 9/68
[52] U.S. Cl. ........................ 424/440; 424/434; 424/435; 424/441; 424/484
[58] Field of Search ........................... 424/440, 434.5, 424/441, 484

[56] References Cited

U.S. PATENT DOCUMENTS

| | | | |
|---|---|---|---|
| D. 93,287 | 9/1934 | Reed | D1/102 |
| 109,677 | 11/1870 | Seitz | 99/138 |
| D. 117,455 | 11/1939 | Parr | D1/102 |
| D. 117,456 | 11/1939 | Parr | D1/102 |
| 122,507 | 1/1872 | Wills | 424/440 |
| 1,430,642 | 10/1922 | Gross | 99/138 |
| 1,593,858 | 7/1926 | Venable | 99/138 |
| 1,847,415 | 3/1932 | Snell | 99/138 |
| 1,915,614 | 6/1933 | Parker | 99/138 |
| 1,971,560 | 8/1934 | Guyon | 90/16 |
| 2,096,611 | 10/1937 | Ellestad | 99/183 |
| 2,208,120 | 7/1940 | Coleman | 107/82 |
| 2,246,778 | 6/1941 | Cahoon | 99/138 |
| 2,295,042 | 9/1942 | Llewellyn | 43/34 |
| 2,323,656 | 7/1948 | Helfenstein | 43/36 |
| 2,388,533 | 11/1945 | Edmondson et al. | 128/202 |
| 2,469,589 | 5/1949 | Barricini | 99/138 |
| 2,488,272 | 11/1949 | Davis | 57/154 |
| 2,499,734 | 3/1950 | Edmondson et al. | 128/197 |
| 2,508,560 | 5/1950 | Adams | 43/36 |
| 2,553,446 | 5/1951 | Edmondson et al. | 128/188 |
| 2,857,908 | 10/1958 | Cornfield | 128/15 |
| 2,897,624 | 8/1959 | Yakel et al. | 43/36 |
| 2,915,061 | 12/1959 | Edmondson et al. | 128/188 |
| 2,926,121 | 2/1960 | Hobbs et al. | 99/138 |
| 2,963,404 | 12/1960 | Hammer et al. | 167/82 |
| 3,114,642 | 12/1963 | Meisel | 99/134 |
| 3,169,907 | 2/1965 | Heusser et al. | 99/138 |
| 3,172,179 | 3/1965 | Schafer | 24/91 |
| 3,192,924 | 7/1965 | Edmondson et al. | 128/188 |
| 3,210,247 | 10/1965 | Suranyi | 99/138 |
| 3,264,115 | 8/1966 | Davis | 99/138 |
| 3,271,256 | 9/1966 | Frey | 167/82 |
| 3,341,414 | 9/1967 | Cherkas et al. | 167/82 |
| 3,344,030 | 9/1967 | Stevens et al. | 99/138 |
| 3,399,673 | 9/1968 | Jones et al. | 128/188 |
| 3,418,743 | 12/1968 | Halvorsen | 43/35 |
| 3,429,308 | 2/1969 | Russell | 99/138 |
| 3,438,787 | 4/1969 | DuRoss | 99/134 |
| 3,444,858 | 5/1969 | Russell | 128/260 |
| 3,493,652 | 2/1970 | Hartman | 99/138 |
| 3,556,811 | 1/1971 | Smith | 99/134 |
| 3,622,352 | 11/1971 | Daylor, Jr. | 99/166 |
| 3,697,641 | 10/1972 | Ahrens | 424/38 |
| 3,738,845 | 1/1973 | Liebrand | 99/134 |
| 3,797,494 | 3/1974 | Zaffaroni | 128/268 |
| 3,816,953 | 6/1974 | Hameen-Anttila | 43/35 |
| 3,867,927 | 2/1975 | Hergott | 128/15 |
| 3,907,811 | 9/1975 | Janssen et al. | 260/293.77 |
| 3,907,813 | 9/1975 | Janssen et al. | 260/293.77 |
| 3,943,928 | 3/1976 | Lariccia et al. | 128/260 |
| 3,966,940 | 6/1976 | Pachter et al. | 424/260 |

(List continued on next page.)

FOREIGN PATENT DOCUMENTS

| | | |
|---|---|---|
| 7830055 | 5/1979 | European Pat. Off. . |
| 83306077.5 | 9/1984 | European Pat. Off. . |
| 86303128.2 | 5/1986 | European Pat. Off. . |
| 7833155 | 11/1978 | France . |
| 132404 | 9/1978 | Germany . |
| 100714 | 8/1981 | Japan . |
| 118511 | 7/1982 | Japan . |
| 1083896 | 9/1967 | United Kingdom . |
| 1171691 | 11/1969 | United Kingdom . |
| 2108841 | 5/1983 | United Kingdom . |

OTHER PUBLICATIONS

Dyer, "Medicated Candies" 1 Q.S. 4 (1953).
Brown, "Absorption of Analgesics from the Buccal Mucous Membrane," 196, The Practitioner 125 (1966).
Beckett et al., "Buccal Absorption of Basic Drugs and its Application as an In Vivo Model of Passive Drug Transfer Through Lipid Membranes," 19 J. Pharm. Pharmac. 31S (1967).

(List continued on next page.)

*Primary Examiner*—D. Gabrielle Phelan
*Attorney, Agent, or Firm*—Workman, Nydegger & Seeley

[57] ABSTRACT

The present invention is directed to methods and compositions for noninvasively administering drugs in a dose-to-effect manner to produce a cardiovascular or renal vascular activity. A cardiovascular or renal vascular drug, which is capable of absorption through mucosal tissues of the mouth, pharnyx, and esophagus is incorporated into a matrix which is in the form of a lollipop. A patient is put at ease when given the lollipop, and the drug rapidly enters the patient's bloodstream as the lollipop is sucked. When treating the patient, the physician can observe the patient's condition and remove the lollipop when it has had a desired effect on the patient. A lollipop into which a cardiovascular or renal vascular drug has been dispersed is particularly useful for achieving rapid vasodilating, calcium channel blocking, beta-blocking, seritonin receptor blocking, angina blocking, antihypertensive, and cardiac stimulating effects and for controlling urine output.

26 Claims, No Drawings

U.S. PATENT DOCUMENTS

| | | | |
|---|---|---|---|
| 3,993,762 | 11/1976 | Langbein et al. | 424/267 |
| 3,996,934 | 12/1976 | Zaffaroni | 128/268 |
| 4,053,604 | 10/1977 | Jaramillo | 424/258 |
| 4,060,084 | 11/1977 | Chandrasekaran et al. | 128/260 |
| 4,093,709 | 6/1978 | Choi et al. | 424/19 |
| 4,131,648 | 12/1978 | Choi et al. | 424/22 |
| 4,138,344 | 2/1979 | Choi et al. | 252/1 |
| 4,139,627 | 2/1979 | Lane et al. | 424/267 |
| 4,168,308 | 9/1979 | Wretlind et al. | 99/138 |
| 4,169,885 | 10/1979 | Raaf et al. | 99/138 |
| 4,225,627 | 9/1980 | Moore | 426/548 |
| 4,226,848 | 10/1980 | Nagai et al. | 99/138 |
| 4,229,447 | 10/1980 | Porter | 424/244 |
| 4,241,092 | 12/1980 | Halik et al. | 426/96 |
| 4,292,299 | 9/1981 | Suzuki et al. | 99/138 |
| 4,307,075 | 12/1981 | Martin | 424/28 |
| 4,311,722 | 9/1982 | Vink et al. | 426/660 |
| 4,346,709 | 8/1982 | Schmitt | 128/260 |
| 4,366,159 | 12/1982 | Magruder | 424/260 |
| 4,369,172 | 1/1983 | Schor et al. | 424/19 |
| 4,372,942 | 2/1983 | Cimiluca | 424/16 |
| 4,389,393 | 6/1983 | Schor et al. | 424/19 |
| 4,390,520 | 6/1983 | Nagai et al. | 424/28 |
| 4,452,825 | 6/1984 | Klacik et al. | 426/658 |
| 4,466,953 | 8/1984 | Keith et al. | 424/28 |
| 4,470,962 | 9/1984 | Keith et al. | 424/28 |
| 4,482,534 | 11/1984 | Blank | 424/28 |
| 4,485,087 | 11/1984 | Otsuka et al. | 424/28 |
| 4,515,769 | 5/1985 | Merritt | 424/49 |
| 4,517,173 | 5/1985 | Kizawa et al. | 99/138 |
| 4,529,589 | 7/1985 | Davydov et al. | 99/138 |
| 4,551,329 | 11/1985 | Harris et al. | 424/22 |
| 4,572,832 | 2/1986 | Kigasawa et al. | 99/138 |
| 4,588,580 | 5/1986 | Gale et al. | 424/21 |
| 4,599,342 | 7/1986 | LaHann | 514/282 |
| 4,642,231 | 2/1987 | Peters et al. | 424/15 |
| 4,668,523 | 5/1987 | Begleiter | 426/104 |
| 4,671,953 | 6/1987 | Stanley et al. | 424/440 |
| 4,692,339 | 9/1987 | Stetson et al. | 426/72 |
| 4,695,463 | 9/1987 | Yang et al. | 424/440 |
| 4,749,575 | 6/1988 | Rotman | 424/441 |
| 4,753,800 | 1/1988 | Mozda | 424/440 |
| 4,755,386 | 7/1988 | Hsiao et al. | 424/435 |
| 4,764,378 | 8/1988 | Keith | 424/435 |
| 4,847,090 | 7/1989 | Della Posta et al. | 424/440 |
| 4,863,737 | 9/1989 | Stanley et al. | 424/440 |
| 4,885,173 | 12/1989 | Stanley et al. | 424/440 |

OTHER PUBLICATIONS

Dearden et al., "Buccal Absorption as a Parameter of Analgesic Activity of Some P-substituted Acetanilides," 23 Journal Pharm, Pharmac. 73S (1971).

Dearden et al., "A New Bucaal Absorption Model," 23 J. Pharm. Pharmac. 68S (1971).

Dollery et al., "Differences in the Metabolism of Drugs Depending Upon Their Routes of Administration," 179 Annals of the New York Academy of Sciences 108 (1971).

Dobkin, "Buprenorphine Hydrochloride: Determination of Analgesic Potency," 24 Canadian Anesthesiology Society Journal 186 (1977).

Kirk–Othmer, 4 Encyclopedia of Chemical Technology 3d Ed., pp. 914–925 (1978).

Edge et al., "Analgesic Effects of Sublingual Buprenorphine," 34 Anaesthesia 463 (1979).

Fry, "Relief of Pain After Surgery," 34 Anaesthesia 549 (1979).

Braunwald, "Introduction: Calcium Channel Blockers," 46 The American Journal of Cardiology, pp. 1045–1045 (Dec. 1980).

Antman et al., "Calcium Channel Blocking Agents in the Treatment of Cardiovascular Disorders, Part I and Part II," 93 Annals of Internal Medicine, pp. 875–900 (1980).

Bullingham et al., "Sublingual Buprenorphine Used Postoperatively: Clinical Observations and Preliminary Pharmocokinetic Analysis," 12 Br. J. Clin. Pharmac. 117 (1981).

Hug et al., "The Pharmacokinetics of Fentanyl," Janssen Pharmaceutica, Inc. (1981).

Ellis et al., "Pain Relief After Abdominal Surgery–A Comparison of I. M. Morphine, Sublingual Buprenorphine and Self–Administrated I.V. Pethidine," 54 Br. J. Anaesth. 421 (1982).

Port et al., "Carfentanil: The Primate Experience," American College of Veterinary Anesthesiolgiests (1983).

Port et al., "Topical Narcotic Anesthesia," 59 Anesthesiology (1983).

Abrams, "New Nitrate Delivery Systems: Buccal Nitroglycerin," vol. 105 American Heart Journal, pp. 848–854 (May 1993).

Windholz et al., "The Merck Index," published by Merck & Co., Inc. pp. 575, 795, 796 and Appendix 3 (1983).

Eleven articles from The First North American Nitroglycerin Symposium, The American Journal of Medicine (Jun. 27, 1983).

White et al., "Comparative Pharmacology of Intravenous Anesthetics–A Model for Determining Dosage Requirements and Therapeutic Concentration Ranges During Surgery," 59 Anesthesiology, A379 (Sep. 1983).

Stanley et al., "The Effect of Population Habits on Side Effects and Narcotic Requirements During High–Dose Fentanyl Anaesthesia," 31 Can Anaesth. Soc. J. 398 (1984).

Derbyshire et al., "Non–Parenteral Postoperative Analgesia," Anesthesia 39, pp. 324–328 (1984).

Border, "Recent Advances in Beta–blocker Therapy for Hypertension," vol. 19 Hosp. Formul. pp. 1120–1126 (Dec. 1984).

DeBoer et al., "Drug Absorption by Sublingual and Rectal Routes," 56 British Journal of Anaesthesiology 69 (1984).

Asthana et al., "Verapamil Disposition and Effect on PQ–Intervals After Buccal, Oral and Intravenous Administration," Arzneim.–Forsch./Drug Res., pp. 498–502 (1984).

Bell et al., "Buccal Morphine–A New Route for Analgesia?" The Lancet 71 (1985).

Bailey et al., "Anesthetic Induction with Fentanyl," 64 Anesth Analg 48 (1985).

Stanley et al., "Management of Pain and Pain–related Problems in the Critically Ill Patient," in Critical Care, State of the Art, vol. 6 (1985).

Huttel et al., "Sublingual Flunitrazepam for Premedication," Acta Anaesthesiol Scand. 29, pp. 209–211 (1985).

Risbo et al., "Sublingual Buprenorphine for Premedication and Postoperative Pain Relief in Orthopedic Surgery," Acta Anaesthesiol Scand. 29, pp. 180–182 (1985).

Schechter et al., "Status of Pediatric Pain Control: A Comparison of Hospital Analgesic Usage in Children and Adults," 77 Pediatrics 11 (1986).

Bailey et al., "Pharmacology of Intravenous Narcotic Anesthetics," in Anesthesia 2nd ed. (Miller ed. 1986).

Su, "Intranasal Delivery of Peptides and Proteins," Pharmacy International (Jan. 1986).

Rothchild, "Are Sick Kids Treaded Properly for Pain?", USA Today, Jan. 28, 1986.

Newsletter "Administration of Nifedipine to NPO Patients," vol. 21 Hospital Pharmacy, pp. 789, 790, and 795 (Aug.

1986).

Forbes et al., "2% Rectal Methohexital for Induction of Anesthesia in Children," vol. 65 Anesthesiology No. 3, (Sep. 1986).

"New Drugs/Drug News," Hospital Therapy, pp. 9, 10, and 15 (Nov. 1986).

Davis, "Parenteral Therapy Techniques–abstracts," Hospital Pharmacy, vol. 21, pp. 1171–1178 (Dec. 1986).

Johnston et al., "the Use of Rectal Clonidine in the Perioperative Period," 64 Anesthesiology, pp. 288–290 (1986).

Saks, "The Cardiovascular Drug Market: Major New Products in Your Future," U.S. Pharmacist, pp. 44, 47–48, 51, 54 and 69 (Jan. 1987).

Tanaka et al., "Oral Nifedipine Treatment for Severe Hypertension," Abstracts, vol. 22, Hosp. Formul, pp. 203–204 (Feb. 1987).

"Personalized Dosing and Effective Drugs Can Control Emesis," Pharmacy Practice News, p. 11 (Mar. 1987).

"Administration of Drugs by The Buccal Route," The Lancet, pp. 666–667 (Mar. 21, 1987).

Lee, "Ophthalmic Delivery of Peptides and Proteins," Pharmaceutical Technology, pp. 26–38 (Apr. 1987).

Mecklenburg, "Insulin Pump Therapy 1987," Practical Diabetology, vol. 6, No. 2, pp. 1–7 (Mar./Apr. 1987).

Grover et al., "Low–dose Intranasal Nitroglycerin Attenuates Pressor Response," 66 Anesthesiology, p. 722 (1987).

Alder et al., "Management of Perioperative Hypertension Using Sublingual Nifedipine," 146 Arch Intern Med. 1927–1930 (1986).

Houston, "Treatment of Severe Hypertension and Hypertensive Crises with Nifedipine," M.C., 146 West J. Med. 701–704, (Jun. 1987).

Dequattro, "Treating Hypertensive Crises: Which Drug for Which Patient?" v., 2:7 The Journal of Critical Illness, 24–35 (Jun. 1987).

Newspaper Article Entiled, "Insulin Shots May Soon be Replaced by a Nasal Spray," UPI (Friday, Sep. 26, 1986).

Fozard et al., "A Controlled Clinical Trial of Oral Droperidol and Droperidol Plus Diazepam for Premedication in Children," Chemical Abstracts, vol. 88, p. 44, 88:83663J (1978) of Brit J. Annesth 49(11): 1147–1151 (1977).

T. H. Stanley, "Oral Transmucosal Fentanyl Citrate (Lollipop) Premedication in Human Volunteers," Anesthesia and Analgesia, vol. 69, No. 1, pp. 21–27 (Jul. 1989).

METHODS AND COMPOSITIONS FOR NONINVASIVE DOSE-TO-EFFECT ADMINISTRATION OF DRUGS WITH CARDIOVASCULAR OR RENAL VASCULAR ACTIVITIES

RELATED APPLICATION

This application is a continuation of pending U.S. application Ser. No. 08/209,113, filed Mar. 3, 1994, now abandoned; for METHODS AND COMPOSITIONS FOR NONINVASIVE DOSE-TO-EFFECT ADMINISTRATION OF DRUGS WITH CARDIOVASCULAR OR RENAL VASCULAR ACTIVITIES, which is a continuation of U.S. application Ser. No. 08/090,485, filed Jul. 12, 1993, for METHODS AND COMPOSITIONS FOR NONINVASIVE DOSE-TO-EFFECT ADMINISTRATION OF DRUGS WITH CARDIOVASCULAR OR RENAL VASCULAR ACTIVITIES, now abandoned, which is a continuation of U.S. application Ser. No. 07/732,723, filed Jul. 18, 1991, for METHODS AND COMPOSITIONS FORNONINVASIVE DOSE-TO-EFFECT ADMINISTRATION OF DRUGS WITH CARDIOVASCULAR OR RENAL VASCULAR ACTIVITIES, now abandoned, which is a continuation of pending U.S. application Ser. No. 07/421,068, filed Oct. 13, 1989, now abandoned, for METHODS AND COMPOSITIONS FORNONINVASIVE DOSE-TO-EFFECT ADMINISTRATION OF DRUGS WITH CARDIOVASCULAR OR RENAL VASCULAR ACTIVITIES, which is a divisional of U.S. application Ser. No. 07/060,046, filed Jun. 8, 1987, for METHODS AND COMPOSITIONS FOR NONINVASIVE DOSE-TO-EFFECT ADMINISTRATION OF DRUGS WITH CARDIOVASCULAR OR PENAL VASCULAR ACTIVITIES, now issued as U.S. Patent Ser. No. 4,885,173, Dec. 5, 1989 which is a continuation-in-part application of copending patent application Ser. No. 06/729,301 filed May 1, 1985, in the names of the inventors hereof, and entitled "METHODS AND COMPOSITIONS FOR NONINVASIVE ADMINISTRATION OF SEDATIVES, ANALGESICS, AND ANESTHETICS," now U.S. Letters Pat. No. 4,671,953, which issued Jun. 9, 1987. That application is incorporated herein by specific reference.

THE FIELD OF THE INVENTION

The present invention is related to methods and compositions for use in systemically delivering potent pharmacological agents having cardiovascular activities to patients in a dose-to-effect manner. More particularly, the present invention is directed to methods and compositions for noninvasive administration of precise doses of potent pharmacological agents having cardiovascular functions (such as vasodilating, calcium channel blocking, beta-blocking, seritonin receptor blocking, angina blocking, anti-hypertensive, and cardiac stimulating properties) and renal vascular functions (such as increasing urine output).

3. The Prior Art

The proper functioning of a person's cardiovascular system determines to a large extent the quality of life that person will enjoy. There have been significant advances in recent years in understanding the complex mechanisms which control the cardiovascular system. This has led to the development of a host of potent new drugs available for clinical use in treating cardiovascular conditions such as congestive heart failure, hypertension, angina, ventricular and atrial fibrillation, and related conditions, and current expectations are that additional potent drugs will continue to become available in the future.

For example, the physician has at his disposal a vast array of hypotensive drugs useful for treating high blood pressure. Blood pressure ("BP") is the product of two hemodynamic factors, cardiac output ("CO") and total peripheral resistance ("TPR"):

$$BP = CO \times TPR$$

A reduction in blood pressure can occur only with a reduction in either CO or TPR, or both.

It is believed that beta-blockers, such as esmolol, nadolol, pindolol, and timolol, reduce blood pressure by decreasing the heart rate or cardiac output. Some beta-blockers, such as atenolol and metoprolol, are known as cardioselective beta-blockers because they have a greater affinity for the $beta_1$ adrenoceptors that predominate in the heart than for the $beta_2$ receptors that predominate in, the bronchi and peripheral vasculature. The cardioselective nature of these beta-blockers is lost if too great a dose is administered.

All beta-blockers, however, if administered in excess, may result in impaired pulmonary function, wheezing, and asthmatic attacks. In addition, there may be serious adverse cardiovascular effects from the use of beta-blockers, such as bradycardia (abnormally slow heart rate), profound hypotension, and even precipitation of severe congestive heart failure. Adverse central nervous system ("CNS") effects of beta-blockers include dizziness, fatigue, mental depression, and in some cases hallucinations; short-term memory impairment and vertigo have also been observed. There may also be adverse gastrointestinal ("GI") reactions, such as diarrhea and nausea.

As a result, it will be appreciated that while beta-blockers have a very valuable place in cardiac treatment, it is critical that the appropriate dosage be given to a patient in order to avoid the dangers and problems caused by overdosing or underdosing.

Other hypotensive drugs, such as nitroprusside and hydralazine, reduce blood pressure by lowering the total peripheral resistance by direct vasodilation. These drugs are particularly potent and are usually given in an emergency or when other hypotensive treatments have failed. Even slight overdoses of this type of hypotensive drug may result in headache, tachycardia, nausea, and diarrhea, and may even precipitate angina pectoris or ventricular arrhythmia.

Still other hypotensive drugs, such a prazosin, are $alpha_1$-blockers which are also capable of reducing blood pressure by lowering the total peripheral resistance as a result of vasodilating effects. An overdose of prazosin may result in headache, drowsiness, palpitation, nausea, and even fainting.

Labetolol is a unique hypotensive drug which combines the features of alpha-blockers with beta-blockers. Blood pressure is reduced due to a decrease in systemic vascular resistance, but usually without a substantial reduction or increase in heart rate, cardiac output, or stroke volume. Unfortunately, labetolol shares the toxic potentials of both the beta and the alpha-blocking agents. In particular, labetolol overdose may promote or exacerbate congestive heart failure, bronchospasm, hypotension, and bradycardia.

Other hypotensive drugs, such as methyldopa and clonidine, inhibit sympathetic vasomotor centers thereby reducing peripheral sympathetic nervous system activity, blood pressure, and heart rate with little change in total peripheral resistance. An overdose of these drugs may result in drowsiness, headache, nausea, dry mouth, palpitation and tachycardia, bradycardia, congestive heart failure, rash, impotence, hepatic abnormalities, and muscle cramps.

Some hypotensive drugs, such as captopril and enalapril, reduce blood pressure by suppressing the renin-angiotensin-aldosterone ("RAA") system. These drugs inhibit the angiotensin-converting enzyme ("ACE") thereby resulting in arterial and possibly venous dilation. Thus, blood pressure is reduced by decreasing the total peripheral resistance with either no change or an increase in heart rate, stroke volume, or cardiac output.

These ACE-inhibiting drugs, if administered in excess, may also result in neutropenia, an abnormally low white blood cell count, which may further lead to systemic or regional infections and possible death. Other adverse effects from overdosing of ACE inhibitors include proteinuria (an abnormally high amount of protein in the urine), rash, taste impairment, excessive hypotension, tachycardia, angina, palpitations, and even myocardial infarction and congestive heart failure.

The physician also has at his disposal a large number of vasodilating drugs useful for treating angina, congestive heart failure, vasospasm, and in some cases hypertension. However, each of these vasodilating drugs also has serious side effects which present dangers when the proper dose for the patient is not given.

For instance, calcium channel blockers (such as diltiazem, nifedipine, and verapamil) dilate the coronary and systemic arteries. This is accomplished by inhibiting the transmembrane influx of extracellular calcium ions across the membranes of the myocardial cells and vascular smooth muscle cells. Calcium plays important roles in the excitation-contraction coupling process of the heart and the vascular smooth muscle cells and in the electrical discharge of the specialized conduction cells of the heart.

Nevertheless, despite their advantages, an overdose of a calcium channel blocker may lead to bradycardia, asymptomatic asystole, hypotension, congestive heart failure, anorexia, nausea, and hallucinations.

Organic nitrates relax vascular smooth muscles. They are particularly useful for relief of angina pectoris, for prophylactic management of situations likely to provoke angina attacks, and for long-term prophylactic management of angina pectoris. Isosorbide may be administered sublingually, lingually, buccally, nasally, or orally. However, an overdose of isosorbide may result in headache, dizziness, nausea, tachycardia, hypotension, fainting, or other dangerous depressions of vital body functions.

Finally, the physician has at his disposal a number of cardiac drugs useful for treating ventricular fibrillation, acute ventricular arrhythmias, and congestive heart failure. Again, these drugs, while useful, can be very dangerous when the patient's susceptibility to the drug makes it difficult to know the proper dose.

Amrinone, for example, is an inotropic drug which increases the force and velocity of myocardial systolic contraction. In addition, amrinone has vasodilatory activity affecting vascular smooth muscle. In patients with congestive heart failure, amrinone produces substantial increases in cardiac output.

However, serious adverse effects may arise in the event of an overdose of amrinone; these adverse effects include: thrombocytopenia (an abnormal decrease in the number of blood platelets), arrhythmias, hypotension, nausea, vomiting, diarrhea, hepatotixicity marked by abnormal liver function, and hypersensitivity.

Bretylium and lidocaine are well-known anti-arrhythmic drugs. Bretylium is used in the prophylaxis and treatment of ventricular fibrillation. However, because it commonly causes hypotension, and may increase ventricular irritability, bretylium is considered a second choice drug. Lidocaine is a CNS-depressing drug which controls ventricular arrhythmias. It also produces sedative, analgesic, and anti-convulsant effects. Overdoses may result in seizures, respiratory arrest, dizziness, nausea, unconsciousness, or even coma.

In addition to drugs for treating cardiovascular conditions, many new drugs for treatment of renal vascular functions have been developed in recent years. However, like most drugs affecting the cardiovascular system, the drugs affecting the renal vascular system must be precisely administered to avoid serious side effects or the dangers of overdosing and underdosing.

Dopamine is a very useful drug for increasing renal blood flow and urine output. Its application is most beneficial in a patient who has a Foley catheter in his uninary bladder. In its clinical application, dopamine is administered until urine output is significantly increased or approaches a normal range.

Despite its benefits, the detriment of using too much dopamine is reflected in increases in the heart rate, blood pressure, cardiac output, and myocardial oxygen consumption. These effects are extremely dangerous in patients with ischemic cardiac disease. Hence, precise dosage control is critical to the effective use of dopamine.

Despite the tremendous advances in the field of pharmacology, physicians continue to administer these new cardiovascular and renal vascular drugs using substantially the same techniques that have been employed for many decades.

Thus, almost all cardiovascularly and renal vascularly active pharmacological drugs continue to be administered via two routes, the oral dosage form for absorption through the stomach and/or intestines or by intramuscular or intravenous injection. These two drug administration modalities are the most frequently used despite the fact that both of these routes suffer from significant disadvantages in particular situations.

The simplest and most prevalent administration route is the oral dosage form. To use this method, a pharmacological drug is incorporated into a tablet, a capsule, or into a liquid base. The patient then ingests the predetermined dose of the drug. Oral administration of a drug is extremely convenient, and, for many drugs, it will continue to be the method of choice. Such administration is non-threatening and is painless to the patient. For most patients, it is also very simple.

Nevertheless, oral administration of a drug suffers from the disadvantage that many patients, particularly geriatric patients, frequently have difficulty swallowing pills. Such patients often refuse to cooperate in swallowing a liquid medication. Even more importantly, absorption of a drug into the bloodstream after swallowing a tablet varies from patient to patient and in the same patient from time to time. The absorption of the drug is dependent upon the movement of the drug from the stomach to the small and large intestines and the effect of secretions from these organs.

Even more important, there is typically a substantial delay between the time of oral administration of a drug and the time that the drug begins to have the desired therapeutic effect on the patient's cardiovascular, renal vascular, or other systems. Generally, a drug must pass from the stomach into the small and large intestines before it will be absorbed into the patient's bloodstream; unfortunately, this typically takes forty-five minutes or longer. For many clinical situations, such a delay is unacceptable.

Further, many drugs taken orally, particularly cardiovascular-acting drugs, are metabolized almost immediately—they are removed from or rendered ineffective by the patient's system before they can have any therapeutic effect.

This occurs because the veins from the small and large intestines, and to a certain extent also the stomach, drain into the liver. Thus, drugs entering the patient's bloodstream through the intestines immediately pass through the patient's liver before distribution throughout the remainder of the patient's body.

Unfortunately, upwards of sixty percent of a drug and essentially one hundred percent of certain drugs) may be removed from the patient's bloodstream during this "first pass" through the liver. The result is that the oral route of administration is impractical for many drugs, particularly many cardiovascular-acting and renal vascular-acting drugs.

Further, additional stress is placed on the liver as it removes the excess drug from the bloodstream. This is particularly severe if the cardiovascular or renal vascular treatment has been occurring over an extended period of time. The liver may become overloaded with the drug's metabolite which then must be excreted in the patient's urine. As a result, there is an increased risk of hepatic or renal disorders.

Yet a further difficulty encountered when administering cardiac and related drugs orally is that dosages are prepared or determined for use with an "average" patient. This is entirely acceptable for many drugs, but some drugs, such as those that have a cardiovascular, anti-hypertensive, vasodilating, anti-anginal, or renal vascular effect, have a widely varying effect on different patients, depending upon individual variations in susceptibility to the particular drug utilized.

Underdosing a patient because of a low susceptibility to the drug fails to revoke the cardiovascular or renal vascular response sought by the physician. Overdosing the patient can result in too much vasodilation, hypotension, cardiac or respiratory depression, other side effects such as headaches, nausea, or other dangerous depression of vital body functions.

Moreover, the slow and uncertain response time for the onset of an observable reaction to a cardiovascular drug when taken orally makes it even more difficult to determine a proper dose for a particular patient; the physician may not learn for an hour, or with some drugs for a few days, whether the patient was underdosed or overdosed. By then, extraordinary measures may be necessary to remedy the patient's condition.

In order to avoid these serious disadvantages inherent in the oral administration route, physicians frequently resort to the injection route for administering many drugs. Injecting a drug (generally intravenously or intramuscularly) results in rapid entry of the drug into the patient's bloodstream and onset of the desired effect. In addition, this type of delivery avoids the removal of large quantities of the drug by the patient's liver that accompanies oral administration. Rather, the drug becomes rapidly distributed to various portions of the patient's body before exposure to the liver; thus, the drug is removed by the liver only after it has first reached the cardiovascular or renal vascular systems.

Most patients have at least some aversion to receiving injections. In some patients, this aversion may be so pronounced as to make the use of injections of serious concern to the physician. Since intense psychological stress can exacerbate a patient's debilitated condition, it sometimes becomes undesirable to use injections where the patient is seriously ill, suffers from a debilitating condition or injury, or where there is no immediate medical assistance.

To compound the problem facing a physician, the individual variation in susceptibility and metabolism with respect to cardiovascular drugs, which makes it difficult to select an appropriate dose for oral administration is even more profound when utilizing the injection route. This is because smaller doses have an increased effect due to the rapidity in which the drug enters the bloodstream because large portions of the drug are not immediately metabolized by the liver.

In order to prevent overdosing a patient with potent cardiovascular drugs, a prudent physician typically injects a patient with a lower than average dose, and later supplements the dose with additional injections as they appear necessary. This, of course, makes necessary the use of repeated injections, which in turn greatly increases the stress on the patient. It is not uncommon for a patient to come to fear that it is time for yet another injection every time the patient sees a member of the hospital staff, which is often the case for those most in need of potent drugs.

Because of the problems associated with the oral and injection routes of administration, physicians have sought other delivery mechanisms for achieving the desired cardiovascular or renal vascular action. Accordingly, transdermal and transmucosal (including buccal, lingual and sublingual) delivery routes have been explored. Those approaches are more pleasant than intramuscular delivery systems and are more reliable since they are less susceptible to gastrointestinal variability. These alternative medicament administration routes also result in more stable plasma and tissue concentrations of the medicament as it is absorbed by the body.

However, the transdermal and transmucosal delivery routes do not enable precise dose-to-effect compatibility (that is, administering a proper dose until the desire effect is achieved and doing so in a manner that eliminates the variabilities between patients). Moreover, these delivery systems do not easily enable rapid adjustment of plasma or tissue concentrations if clinical conditions dictate that a higher or a lower concentration would be more desirable in the next few minutes.

This is most easily seen with sublingual nitroglycerin tablets used for angina. When a patient has angina, the patient places a nitroglycerin tablet under his tongue (the "sublingual" administration route). From a practical standpoint, it is not possible to remove a sublingual nitroglycerin tablet once it has been placed under the tongue. The tablet is very small (typically, two to three millimeters in diameter) and dissolves very quickly.

In addition, because the tablet dissolves so rapidly, there is a lag time between the time the dose is given (i.e., when the tablet dissolves) and when the effects are observed. So, once it is under the tongue, the patient is more or less committed to taking the entire dose of nitroglycerin contained in the tablet, even if the angina would have been alleviated with only one-half of the dose in a tablet.

Consumption of the remainder of the tablet often results in an overdose and a severe headache. If the first tablet is not effective in treating angina, the patient must then take a second or a third tablet. This is a slow process and still may ultimately result in a relative overdose after the final tablet.

There are other practical problems with the sublingual administration route for nitroglycerin. Sublingual nitroglycerin tablets are intentionally very small in size so that they may be conveniently placed and maintained under the patient's tongue without evoking an undesirable response. However, the small size of the tablet makes them difficult for the patient to handle.

Another approach to overcoming the problems associated with the injection and oral delivery routes has been to incorporate the cardiovascular-acting renal vascular-acting drug into a nasal spray. However, since intermittent, multiple sprays of the drug are required, patients find it difficult to deliver the appropriate dosage to alleviate their symptoms and avoid the problems and side effects of overdosing.

Moreover, the propellant in the spray can interfere with the effectiveness and accurate delivery of the proper dosage of the drug. Problems with the temperature stability of the ingredients and the angle of the sprayer can also affect the dose of drug actually delivered. While these nasal sprays have avoided some of the problems of the oral and injection routes, they have not solved many of the problems associated with the delivery of the precise dose necessary to relieve the symptoms of the patient while accounting for the patient's individual susceptibility to the cardiovascular-acting or renal vascular-acting drug.

For example, sprays incorporating nitroglycerin have been developed in which the drug is sprayed on the oral mucosa using a lingual aerosol canister (the "lingual" administration route). The nitroglycerin lingual aerosol spray delivers nitroglycerin in 0.4 mg metered doses. This in essence is a delivery of a series of 0.4 mg boluses of nitroglycerin, only providing an alternative method of delivery, without any improvement whatsoever in titratability. The dosage options are the same as tablets, i.e., increments of 0.4 mg doses. The dose is preferably sprayed onto or under the tongue and then the mouth is immediately closed. The spray canister delivers a fixed dosage for each spray. As in sublingual administration, lingual administration is relatively fast-acting, but if relief is not attained after the initial spray, additional sprays must be given. Again, this is a slow process which usually results in a relative overdose after the final spray. Moreover, the lingual spray suffers from the same problems as discussed above with respect to the nasal sprays.

Additionally, care must be taken to not shake the aerosol canister prior to use, since shaking may generate bubbles within the canister which impair the proper release of nitroglycerin from the device. Also, the spray should not be inhaled, and swallowing immediately after spraying should be avoided. For many patients, particularly geriatric patients, these administration techniques may be too complex.

Physicians may also recommend buccal administration of nitroglycerin or other cardiovascular-acting or renal vascular-acting drugs. Buccal nitroglycerin tablets are typically placed between the upper lip and teeth. The tablet surface develops a gel-like coating that adheres, to the mucosal surface of the mouth. As long as the tablet remains intact, nitroglycerin continues to pass from the tablet matrix to the mucosal tissue where it is rapidly absorbed. If the tablet is chewed and broken up, an undesirable mount of nitroglycerin is released for submucosal absorption or, if swallowed, the nitroglycerin would be metabolized by the liver as discussed above. Since the nitroglycerin in a buccal tablet can enter the body in three different areas, depending upon whether the tablet remains in place or is chewed, it is often difficult to ensure that the proper dose is delivered.

When used properly, buccal nitroglycerin acts rapidly after placement in the mouth-almost as fast as sublingual nitroglycerin. Nitroglycerin is released into the buccal cavity so long as the tablet remains intact. The average tablet dissolution time is between three to five hours; therefore, many patients, particularly geriatric patients, will have difficulty keeping the tablet in place for so long. Tablet dissolution time and the effective amount of the medicament delivered to the patient varies from patient to patient, and even in a given patient, because of differences in saliva production, tongue manipulation, inadvertant chewing (displacement of the gel "seal"), and eating or drinking by the patient.

Because of the wide variation of dissolution times from patient to patient, the same buccal nitroglycerin tablet is likely to result in either an overdose or underdose, depending on the patient. Although it is theoretically possible to manually remove the buccal tablet from the mouth and later replace it so as to control the amount of nitroglycerin released to the patient, such a procedure is not very practical.

For instance, if the tablet is manually removed from the mouth by the patient, it is likely to become contaminated by the patient's touch. Further, many patients who need nitroglycerin medication are older; these patients have difficulty coordinating small tablets in their mouth and find it extremely difficult to handle the small tablets with their hands.

Another alternative method of administering cardiovascular-acting or renal vascular-acting drugs is by applying ointment or patches to the skin which contain the drug. For example, nitroglycerin will readily pass through the skin (the "transdermal" administration route) and into the patient's bloodstream. When ointment is applied to the skin, its effect is observed within sixty minutes, with a duration from four to eight hours. Nitroglycerin patches are designed to provide continuous treatment for up to 24 hours.

The effect of nitroglycerin ointment varies from patient to patient. The area of application of the dose as well as the site, dosage, state of hydration of the skin surface, and permeability are all variables affecting the patient's response. In addition, nitroglycerin ointment is impractical for many patients because of the difficulty in application, its mess, cosmetic problems, and potential staining.

A major advance in cutaneous administration of nitroglycerin occurred with the development of a sustained-release patch. These preparations contain nitroglycerin in a reservoir or matrix and are designed to provide constant delivery of the drug into the circulation for twenty-four hours. The rate of the drug release is primarily determined by the device itself, rather than the characteristics of the patient's skin. However, important questions regarding dosage requirements, efficacy, and duration of action remain unanswered. Several recent reports involving patients with either angina pectoris or congestive heart failure have questioned the efficacy of these products. Several mechanisms have been proposed to account for the variability of patient response. The development of tolerance, low nitroglycerin plasma levels and tissue concentrations secondary to poor absorption of the drug, and inability of the delivery system to deliver drug for a full twenty-four hours are all proposed explanations of-this phenomenon.

Similarly, patients using nitroglycerin transdermal patches may have reasonable plasma and tissue concentrations of nitroglycerin, but they cannot easily or rapidly increase or decrease those concentrations except by pulling off the patches or adding additional patches. Both of the latter processes are, at best, gross adjustments because of the slow response in transdermal patches, which results in relative overdose or underdose of nitroglycerin.

In addition to the problem of slow onset, recent research indicates that continuous use of transdermal patches results in the development of a tolerance to the nitroglycerin. This suggests that continued use of nitroglycerin transdermal patches may not be a practical alternative for many patients.

In view of the foregoing, it will be appreciated that it would be an important advancement in the art of administering cardiovascular, renal vascular and related drugs if suitable methods and compositions could be provided that were capable of rapid action, of avoiding the disadvantage of immediate metabolism through the patient's liver, and of not involving an injection.

Given the life-sustaining importance of the cardiovascular and renal vascular systems, any drug which affects these systems is potentially life threatening if administered improperly. It would be, therefore, a further advancement in the art of administering potent cardiovascular and renal vascular drugs if suitable methods .and compositions could be provided that enabled individual patient fine-tuning of ideal doses (providing a dose-to-effect administration modality) so that doses could be adjusted not only on an individual basis but easily increased or deceased at each time of administration.

It would also be an important advancement in the art if methods and compositions could be provided that would give a physician, as well as the patient (in appropriate circumstances), control over the administration of medication so that a desired effect is not only obtained but also maintained during times when his cardiac status or blood pressure changed.

Such methods and compositions are disclosed and claimed herein.

BRIEF SUMMARY AND OBJECTS OF THE INVENTION

The present invention is directed to novel methods and compositions for use in administering potent cardiovascular and renal vascular related drugs capable of eliciting appropriate cardiac, vasodilating, anti-hypertensive, anti-anginal, renal, and related effects. The present invention is capable of introducing the drug into the patient's bloodstream almost as fast as an injection — and much faster than oral administration. Yet, it is nonthreatening and painless.

These significant advantages are achieved by incorporating into a candy or compressed powder matrix a drug capable of being absorbed through the mucosal tissue found in a patient's mouth, pharynx, and esophagus. The resultant mixture is then advantageously formed into a lollipop, which, as discussed in greater detail hereinafter, can be administered in a dose-to-effect manner.

Even patients having difficulty swallowing a pill or refusing to swallow a liquid, will give little resistance to sucking on a lollipop. When dealing with resistant adults, a lollipop evokes a pleasurable response in the patient and gives the patient something nonthreatening on which to concentrate. Further, sucking is a natural and instinctive response which virtually all persons find relaxing.

A cardiovascular-acting or renal vascular-acting drug administered in this way will quickly enter the patient's bloodstream through the veins which serve the mucosal tissues. Appropriate monitoring of the patient's reaction to the drug (e.g., measuring blood pressure, monitoring heart rate or changes in the EKG, monitoring the extent of angina, observing the degree of vasodilation, or monitoring the urine output) will indicate when the drug has evoked a suitable response. The lollipop may then be removed, or its rate of consumption may be decreased.

It will be appreciated that the ever-present risk of overdosing a patient is substantially.-minimized, if not almost eliminated, through the proper use of the methods and compositions within the scope of the present invention. The rate at which the cardiovascular drug is to be absorbed by the body can be varied by varying the rate the lollipop dissolves. This can be achieved by modifying the composition of the lollipop or the vigor with which the patient "sucks" on the lollipop.

Thus, the drug dose is given over a period of time rather than all at once, and the administration rate can be reduced if such appears necessary. As soon as the patient's blood pressure becomes ideal, heart rate stabilizes, urine output increases to more normal limits, the EKG improves, or angina disappears, he will simply stop sucking the lollipop and/or the physician can easily remove the lollipop from the patient's mouth.

A patient experiencing angina can self-administer small amounts of drug "on demand" by simply licking or sucking on the lollipop in response to his subjective experience of the cardiovascular or renal vascular condition (for example, angina pain, urine output, and heart rate). The patient can then remove the lollipop before the side effects and dangers of overdosing are experienced.

Unlike the use of injections or oral ingestion of cardiovascular medications where a relatively large bolus dose of medication is given intermittently, use of a lollipop can permit the patient to take very small doses of a cardiac or renal drug on an almost continuous basis. Moreover, such administration can be regulated in response to the patient's own need for medication in light of his own subjective experience of the cardiac or renal condition and the patient's own personal susceptibility to the particular drug utilized.

Further, the use of a lollipop to administer cardiovascular-acting or renal vascular-acting drugs is far superior to the presently used transdermal techniques. A nitroglycerin lollipop, for example, can provide near-immediate response, whereas transdermal, nitroglycerin in the form of ointments and patches requires up to an hour before any therapeutic effect is realized. This large lag time between the dose of nitroglycerin received via transdermal techniques and its observable effect prohibits the use of these methods in a true dose-to-effect manner.

In addition, the variation of skin permeability from patient to patient makes it difficult for the physician to prescribe a correct dose for each patient. Skin permeability may vary even in the same patient from time to time. For instance, changes in stress, skin status such as sunburned, dry, or oily skin, and even repeated transdermal administration in the same location all affect skin permeability.

It is, therefore, a primary object of the present invention to provide noninvasive methods and compositions of rapidly reducing heart rate or blood pressure, eliminating angina, increasing urine output, improving the EKG, or inducing an appropriate state of cardiac function.

It is another important object of the present invention to provide methods and compositions that would allow for more physician and patient control over the administration of cardiovascular or renal vascular drug actions so that individual patient differences, susceptibilities, and metabolisms can be taken into account.

Yet another primary object of the present invention is to provide methods and compositions foe drug administration which minimize the psychological trauma generally associated with injections, the adverse physical and psychological problems often associated with the oral administration of potent drugs, and the limitations of the sublingual, lingual, buccal, nasal, and transdermal modalities of drug administrations.

It is a further object of the present invention to provide for methods of drug administration that are capable of dose-to-effect administration, thereby minimizing underdosing and overdosing of the patient.

Still a further object of the present invention is to provide methods and compositions that will permit a patient to control the amount of cardiac medication administered according to individual variations in the susceptibility to the particular medication used and in response to the patient's subjective experience of angina, hypertension, tachycardia, urine output, changes in EKG, etc.

These and other objects and features of the present invention will become more fully apparent from the following description and appended claims.

DETAILED DESCRIPTION OF THE PREFERRED EMBODIMENTS

As discussed above, the present invention is directed to methods and compositions for use in the noninvasive dose-to-effect administration of cardiovascular-acting and renal vascular-acting drugs. Advantageously, the present invention permits exceptional control over the effect of the drug administered, despite individual susceptibility to and metabolism of that drug.

While maintaining the convenience of oral administration, the present invention provides for the advantages of the injection route. At the same time, the present invention avoids the disadvantages identified above with respect to these two traditional routes of administration as well as newer lingual, sublingual, bucal, nasal, and transdermal applications.

A few drugs, such as nifedipine, nitroglycerin, and isosorbide dinitrate, have been administered by absorption through mucosal tissue because the transmucosal route is faster than oral administration modality, and, unlike injections, can be easily self-administered. While drugs are easily given by the transmucosal route, they have not, unfortunately, been given by a dose-to-effect method. In dose-to-effect drug administration, the drug is administered until a predetermined effect is obtained; thereafter, the administration process is modified or terminated.

Despite some limited use, the transmucosal route has not been favored for routine use. Instead, where a delay in drug action is acceptable, the oral route has been preferred by most physicians, and injections have been used where delay is not acceptable.

Transmucosal dose-to-effect delivery of a drug is slightly slower to provide active concentrations of a drug in a patient's system than is the use of an injection. Nevertheless, it has been discovered that the transmucosal route can be adapted so that any loss in the speed of drug uptake is more than offset by the ability to administer the drug noninvasively (much to the appreciation of the patient) and by the ability to control the dose received by the patient.

A drug must be lipophilic in order to be absorbed across mucosal tissue. However, this requirement is not a serious limitation since a large number of drugs are naturally lipophilic or can be provided in a lipophilic form.

In accordance with the present invention, a suitable drug is dispersed or compressed within a carbohydrate mass or other suitable matrix and incorporated into a lollipop. The drug-containing lollipop is then given to a patient to suck on so that the drug will be released into the patient's mouth as the lollipop dissolves. Being lipophilic, a significant portion of the drug is absorbed through the mucosal tissues of the mouth, pharynx, and esophagus.

From the mucosal tissues, the drug rapidly enters the patient's bloodstream. Equally important, the blood in the veins draining from the mouth and the pharyngeal and esophageal regions passes through a substantial portion of the body (so that the drug can be absorbed) before the blood passes through the liver (where the drug will usually be metabolized and/or inactivated).

The use of a drug-containing lollipop to administer a drug offers several important advantages. First, a lollipop is familiar and lacks the menace of a syringe. Being a item normally associated with pleasure, a lollipop immediately evokes a positive psychological response. In addition, the lollipop is easy for the patient or physician to handle.

Importantly, it has been found that the use of drug-containing lollipop can permit the physician to control the dosage of the drug administered to the patient in order to produce the desired anti-anginal state, blood pressure, heart rate, urine output, or changes in EKG, etc., thereby resulting in dose-to-effect drug administration. The use of such drug-containing lollipops also permits the, patient to exert control over the dosage received of cardiac or renal drugs in order to optimize functions of the cardiovascular or renal vascular systems.

These important advantages are available because very small amounts of the drug may be delivered to a patient substantially continuously, and administration of the drug may be halted at any time by simply removing the lollipop from the patient's mouth. This not only allows a physician to monitor a patient's condition so that a particular effect is obtained and maintained, but also provides an important safety benefit.

By contrast, once a typically bolus dose of a drug is given orally, sublingually, lingually, buccally, nasally, transdermally, or by injection, it is either impossible or impractical to retrieve the dose. Thus, the full effects of the administered drug will be felt by the patient. Further, a large dose given every few hours results in wide swings in plasma concentration of the drug, while the use of a lollipop in accordance with the present invention evens out the plasma concentration of that drug.

In practice, a physician can offer the patient a drug-containing lollipop together with simple instructions that the lollipop is to be sucked rather than chewed. Anxious adults are particularly put at ease by this approach. The physician can then monitor the patient's condition to ensure the desired effect is achieved. If, for example, the drug-containing lollipop contains nifedipine, the physician can monitor the patient's angina or blood pressure until a suitable modification of the blood pressure is achieved or the angina has been relieved.

As mentioned above, it is preferred that the medicated matrix material take the form of a lollipop. Use of a stick or other suitable holder permits easy removal of the lollipop when the patient has received the proper dosage of the drug contained in the lollipop.

Provision of a suitable holder also facilitates intermittent administration of the drug to maintain a desired condition and makes it more convenient for a patient to intermittently self-administer a cardiac medication in response to variations in the patient's subjective or objective evaluation of his cardiac condition. Use of a suitable holder prevents contamination of the medicated matrix material when the lollipop is periodically removed from the mouth and later replaced.

The speed at which a sufficient amount of drug enters the patient's bloodstream so as to produce a desired effect depends on several factors. For example, a very potent drug requires fewer drug molecules to enter the patient's system than does a weak drug to produce a desired effect. Accordingly, if rapid modification of cardiovascular action (i.e., an immediate decrease in blood pressure) is desired, a potent rather than a weak drug could be used.

Additionally, the degree of lipophilicity of a drug directly affects the rate of absorption of the drug. A highly lipophilic drug will result in the more rapid onset of a desired response than will a more moderately lipophilic drug.

For example, nitroprusside is a very potent drug which is highly lipophilic. However, nifedipine is nearly twice as lipophilic as nitroprusside and thus is capable of faster absorption. It will be appreciated, however, that other pharmacokinetic properties of a drug will affect the rate at which the effect of the drug is observed in the patient. For example, while isosorbide is not so lipophilic, its other pharmacokinetic properties make it extremely fast-acting once it is absorbed into the bloodstream.

The choice of matrix and the concentration of the drug in the matrix are also important factors with respect to the rate of drug uptake. A matrix that dissolves quickly will deliver a drug into the patient's mouth for absorption more quickly than a matrix that is slow to dissolve. Similarly, a lollipop that contains a drug in a high concentration will release more drug in a given period of time than a lollipop having a low drug concentration.

It will be appreciated that varying the concentrations of the drug in the matrix or the properties of the matrix (particularly the rate at which the matrix dissolves) can be advantageously used in designing specific compositions for specific uses. A lollipop of a given concentration may be used to relieve angina, while a lollipop of a stronger concentration (which is possibly of a different color so as to prevent confusion) can be used when it is desired to decrease arterial blood pressure.

Another use of these properties is to prepare a multilayer lollipop where the outer layer is of a concentration differing from that of the inner layer. Such a drug delivery system has a variety of applications. By way of example, it may be desirable to quickly get a predetermined dose of a drug into the bloodstream to obtain a desired effect and then use a different concentration to maintain that effect.

In addition to modifying the physical characteristics of the lollipop, the technique used by the patient to suck the lollipop may also be used to affect the rate of the absorption of the drug. If substantial portions of the lollipop are chewed and swallowed, the normal complications of oral administration will be encountered (i.e., slow response and loss of drug in the stomach and liver).

If the lollipop is sucked slowly with little production of saliva, very little drug will be swallowed, but a reduction in the amount of saliva will also cause a reduction in the rate at which the medicated candy portion dissolves. It will be appreciated that the technique of sucking utilized by the patient can have a significant effect on the rate of drug uptake into the patient's bloodstream.

Use of a lollipop, in contrast to a simple drop, pellet, or spray, helps control proper placement of the medicated matrix within the patient's mouth since the medical professional can manipulate the matrix and demonstrate proper placement to the patient, and the medical professional can easily monitor placement by observation of the angle of the protruding stick. Once a suitable technique for sucking the lollipop has been selected, the remaining factors can be adjusted accordingly.

It will be appreciated from the foregoing that the present invention has broad applicability to a variety of cardiovascular and renal vascular agents. For example, the present invention may be utilized in the administration of antianginal and vasodilators (such as nitroglycerin and isosorbide), calcium channel blockers (such as diltiazem, verapamil, and nifedipine), beta-blockers (such as esmolol, nadolol, pindolol, timolol, atenolol, and metoprolol), other hypotensive agents (such as prazosin, labetolol, methyldopa, nitroprusside, clonidine, hydralazine, captopril, and enalapril), cardiac drugs (such as bretylium, lidocaine, and amrinone), and renal modification drugs (such as dopamine). It will be appreciated that other drugs may also be utilized within the scope of the present invention. What is important is that the drug be lipophilic, potent, and fast acting.

By incorporating a drug into a lollipop within the scope of the present invention, the amount of the drug used will generally differ from the amount used in more traditional injection and oral administration techniques. Depending upon the lipophilic nature of the drug, its potency, and its end use (e.g., relief of anginal pain, lowering blood pressure, modifying cardiac functions, and modifying urine output), the total concentration of the drug in a typical lollipop may contain up to fifty times the amount of the drug which may be used in an injection. However, for purposes of example, Table I sets forth presently contemplated ranges of the dosages of certain drugs which would typically be used.

TABLE I

| Drug Generic | Lollipop Dose Range |
|---|---|
| Amrinone | 50–100 milligrams |
| Atenolol | 50–150 milligrams |
| Atropine | 0.4–1 milligrams |
| Bretylium | 50–500 milligrams |
| Captopril | 25–75 milligrams |
| Clonidine | 0.1–0.5 milligrams |
| Diltiazem | 30–120 milligrams |
| Dipyridamole | 50–150 milligrams |
| Dopamine | 350–700 micrograms |
| Enalapril | 5–15 milligrams |
| Ephedrine | 25–75 milligrams |
| Esmolol | 25–250 milligrams |
| Hydralazine | 10–75 milligrams |
| Isosorbide | 2.5–40 milligrams |
| Labetolol | 100–400 milligrams |
| Lidocaine | 50–250 milligrams |
| Methyldopa | 250–750 milligrams |
| Metoprolol | 25–100 milligrams |
| Nadolol | 40–160 milligrams |
| Nifedipine | 10–40 milligrams |
| Nitroglycerin | 0.2–1.2 milligrams |
| Nitroprusside | 10–50 milligrams |
| Phenoxybenzamine | 10–40 milligrams |
| Phentolamine | 5–15 milligrams |
| Pindolol | 5–15 milligrams |
| Prazosin | 2–10 milligrams |
| Procainamide | 250–500 milligrams |
| Timolol | 10–50 milligrams |
| Tolazoline | 25–75 milligrams |
| Timethaphan | 10–50 milligrams |
| Verapamil | 80–240 milligrams |

When the drug is dispersed in a "candy" matrix, care must be taken that no decomposition of the drug occurs. Since the candy matrix must typically be heated above about 230° F., this can be a serious limitation to the use of conventional candy-making processes.

Furthermore, one or more of the ingredients necessary for the successful formulation of a hard candy base may have an adverse effect, when in solution, upon the stability of the incorporated therapeutic agent. Therefore, a manufacturing technique may be employed that, where necessary, will enable most therapeutic agents to be incorporated with suitable flavors and other insipients into a solid dosage form on an appliance or holder, for a dose-to-effect modality.

To achieve this, the therapeutic agent is included in a compressible carbohydrate matrix and stamped or directly compressed in an appropriate mold so that the drug-containing matrix is attached to an appliance such as a holder.

Further discussion of these and other manufacturing techniques are found in copending patent application Ser. No. 07/060,045, filed Jun. 8, 1987, in the names of the inventors hereof, and entitled "COMPOSITIONS AND METHODS OF MANUFACTURE OF COMPRESSED POWDER MEDICAMENTS." That application is incorporated herein by specific reference.

The choice of a particular carbohydrate matrix is subject to wide variation. Conventional sweeteners such as sucrose may be utilized, or carbohydrates suitable for use with diabetic patients, such as sorbitol or mannitol, might be employed. Other sweeteners, such as the aspartames, can also be easily incorporated into a composition in accordance with the present invention. The matrix base may be very soft and fast dissolving, or may be hard and slower dissolving. Various forms will have advantages in different situations.

It will be appreciated from the foregoing that the present invention has broad applicability and will be useful in a wide variety of situations. It provides a useful alternative to the traditional routes of administration, and permits the physician extraordinary control over the dosage of the cardiovascular-acting or renal vascular-acting drug that is administered to a patient.

Some of the more important features and advantages of the present invention will be better appreciated and understood by reference to a few illustrative examples:

EXAMPLE 1

The candy matrix or base for the drug-containing lollipop within the scope of the present invention is advantageously prepared utilizing candy preparation formulas and techniques which are known in the prior art. For example, a hard candy base is prepared by dissolving 50 grams of sucrose in 50 grams of water and heating the solution to about 240° F. Next, about 40 grams of corn syrup having a dextrose equivalent of 42 units, and a high maltose content (30%–35% maltose) is added, and the mixture is cooked at about 300° F. to reduce the water content to about three percent (3%). After recooling the thickened candy mass to about 240° F., a suitable oil flavoring (e.g., lemon, cherry, or other flavor) is added.

Concurrently, a solution containing a soluble drug is prepared for incorporation into a candy matrix. In this example, the drug selected is timolol. Timolol is a potent, lipophilic beta-blocker which is useful as an anti-hypertensive and for protecting a patient with post-myocardial infraction. Its high potency and lipophilicity make it an excellent drug for transmucosal administration in accordance with the present invention. A suitable timolol solution is prepared by dissolving 400 milligrams of timolol in four cubic centimeters of sterile water.

This timolol solution is mixed with 32 cubic centimeters of the hot candy mass formed as set forth above, and the resultant mixture is gently mixed as it cools to about 225° F., taking care not to induce formation of air bubbles in the candy mass.

The solution is then poured into suitable molds having a 2.0 cubic centimeter capacity that have been prelubricated with vegetable oil to prevent sticking. A four inch commercially available wax-coated compressed paper stick is next inserted into the base of each mold. The mixture is then permitted to set.

The foregoing procedure results in the preparation of 20 lollipops, each containing 20 milligrams of timolol. This dose is about two times higher than generally given orally.

The physician has at his disposal a large number of vasodilating drugs useful for treating angina, congestive heart failure, vasospasm, and in some cases hypertension. However, each of these vasodilating drugs also has serious side effects which present dangers when the proper dose for the patient is not given.

The examples which follow employ the use of certain vasodilating drugs which act as calcium channel blockers. The calcium channel blockers (such as diltiazem, nifedipine, and verapamil) dilate the coronary and systemic arteries. This is accomplished by inhibiting the transmembrane influx of extracellular calcium ions across the membranes of the myocardial cells and vascular smooth muscle cells. Calcium plays important roles in the excitation-contraction coupling process of the heart and the vascular smooth muscle cells and in the electrical discharge of the specialized conduction cells of the heart.

Nevertheless, despite these advantages, an overdose of a calcium channel blocker may lead to bradycardia, asymptomatic asystole, hypotension, congestive heart failure, anorexia, nausea, and hallucinations.

Thus, it will be appreciated that overdosing the patient with any of these vasodilating drugs may result in serious side effects to the patient which may cause the patient great discomfort and, in some instances, may be so serious as to cause failure of vital organs resulting in death.

The following examples demonstrate methods and compositions for safely administering such vasodilating drugs in a dose-to-effect manner such that the undesirable and dangerous side effects which may result from overdosing of these vasodilating drugs are avoided.

Although the following examples only demonstrate the methods and compositions of the present invention as they relate to specific vasodilating drugs, it will be appreciated that other drugs may also be utilized within the scope of the present invention. What is important is that the drug be lipophilic, potent, and fast-acting so that the desired effects can be observed by the medical professional (or the patient himself if the drug is self-administered) in sufficient time to remove the lollipop from the patient's mouth in time to prevent overdosing. Indeed, any vasodilating drug having the characteristics described above may be administered to a patient according to the present invention.

EXAMPLE 2

In this example, nifedipine is selected for incorporation into a compressed powder lollipop. Nifedipine is a potent lipophilic drug useful for controlling blood pressure, particularly in perioperative hypertension associated with cardiovascular procedures, and for producing controlled hypotension during surgical procedures. Its high potency and lipophilicity make it an excellent drug for transmucosal administration in accordance with the present invention.

A suitable matrix is prepared by combining 200 milligrams of nifedipine, 400 milligrams citric acid, 400 milligrams calcium stearate, 17.7 grams compressible sugar, 17.7 grams maltodextrin, 600 milligrams peppermint microcaps, 1.0 gram cherry microcaps, and 2.0 grams vanilla microcaps. Alloquats of 2000 milligrams each are then hydraulically compressed around a commercially available wax-coated compressed paper holder, using a force sufficient to provide a final volume of 2 cubic centimeters. The foregoing procedure results in the preparation of lollipops, each containing 10 milligrams of nifedipine

EXAMPLE 3

According to the procedure of this example, the dose-to-effect administration of a nifedipine lollipop prepared substantially according to the procedure of Example 2 is illustrated. A patient's blood pressure is taken upon entry into the operating room just before introduction of anesthesia for removal of a gall bladder. The blood pressure is 185/105 mm Hg (increased above a normal of 130/80 mm Hg because of anxiety). A lollipop containing 10 milligrams of nifedipine is given to the patient while the anesthesiologist adjusts other monitoring devices.

In two minutes, blood pressure is 160/95 mm Hg, and a minute later blood pressure is 145/90 mm Hg. Thirty seconds later, the anesthesiologist removes the lollipop (when blood pressure is 132/82 mm Hg) and begins anesthetic induction. Because blood pressure is now normal, anesthetic induction is significantly safer than it would have been if induction had begun only three to four minutes before. In addition, the patient has received just enough nifedipine to obtain the right blood pressure. Care must be taken that too much of the drug is not given, which could reduce blood pressure to dangerously low levels. Alternatively, if too little of the drug is given, the blood pressure will not be reduced enough.

EXAMPLE 4

In the procedure of this example, a patient who is presently experiencing angina is given a drug-containing lollipop, prepared substantially according to the procedure of Example 2, in order to relieve immediately the anginal pain. In this example, nifedipine in a lollipop dose of 10 milligrams is used. The patient experiences some relief within 5 minutes after beginning to suck on the lollipop, and after about 10 minutes the anginal pain is substantially relieved. The nifedipine-containing lollipop is then removed and discarded.

EXAMPLE 5

A drug-containing lollipop in accordance with the present invention is prepared substantially according to the procedure of Example 1, except that the drug nifedipine in a lollipop dose of 10 milligrams is substituted for the timolol. The nifedipine-containing lollipop is used in the procedure set forth in Example 3 for treating a patient with hypertension. As the patient sucks on the candy matrix lollipop, the patient's blood pressure is rapidly lowered to the desired value at substantially the same rates as the compressed powder, nifedipine-containing lollipop of Example 3.

EXAMPLE 6

A drug-containing lollipop in accordance with the present invention is prepared substantially according to the procedure of Example 1, except that the drug nifedipine in a lollipop dose of 10 milligrams is substituted for the timolol. The nifedipine-containing, candy matrix lollipop is used in the procedure set forth in Example 4 for rapid relief from angina. The patient experiences relief within approximately the same time parameters as the compressed powder, nifedipine-containing lollipop of Example 4.

EXAMPLE 7

A drug-containing lollipop in accordance with the present invention is prepared substantially according to the procedure of Example 2, except that the drug diltiazem in a lollipop dose of 30 milligrams is substituted for the nifedipine. The diltiazem-containing lollipop is used in the procedure set forth in Example 3 for treating a patient with hypertension. As the patient sucks on the lollipop, the patient's blood pressure is rapidly lowered to a predetermined value.

EXAMPLE 8

A drug-containing lollipop in accordance with the present invention is prepared substantially according to the procedure of Example 2, except that the drug diltiazem in a lollipop dose of 50 milligrams is substituted for the nifedipine. The diltiazem-containing lollipop is used in the procedure set forth in Example 4, for rapid relief from angina. The patient experiences some relief within 4 minutes, and after about 7 minutes the anginal pain is substantially relieved.

EXAMPLE 9

A drug-containing lollipop in accordance with the present invention is prepared substantially according to the procedure of Example 2, except that the drug verapamil in a lollipop dose of 80 milligrams is substituted for the nifedipine. The verapamil-containing lollipop is used in the procedure set forth in Example 3, for treating a patient with hypertension. As the patient sucks on the lollipop, the patient's blood pressure is rapidly lowered to a predetermined value.

EXAMPLE 10

A drug-containing lollipop in accordance with the present invention is prepared substantially according to the procedure of Example 2, except that the drug verapamil in a lollipop dose of 120 milligrams is substituted for the nifedipine. The verapamil-containing lollipop is used in the procedure set forth in Example 4 for rapid relief from angina. The patient experiences some relief within 5 minutes, and after about 8 minutes the anginal pain is substantially relieved.

EXAMPLE 11

In the procedure of this example, a patient who is presently experiencing supraventricular tachyarrhythmias is given a drug-containing lollipop in accordance with the present invention. The lollipop is prepared substantially according to the procedure of Example 2, except that the drug verapamil in a lollipop dose of 200 milligrams is substituted for nifedipine. Rapid conversion to normal sinus rhythm is observed, and the heart rate goes from about 200 beats per minute to about 80 beats per minute in about 3 minutes. The verapamil-containing lollipop is then removed and discarded.

The following examples describe the preparation and use of a drug-containing lollipop wherein the drug dispersed within the lollipop is a beta-blocker. Some beta-blockers, such as esmolol, nadolol, pindolol, and timolol, reduce blood pressure by decreasing the heart rate or cardiac output. Other beta-blockers, such as atenolol and metoprolol, are known as cardioselective beta-blockers because they have a greater affinity for the beta$_1$ adrenoceptors that predominate in the heart than for the beta$_2$ receptors that predominate in the bronchi and peripheral vasculature. The cardioselective nature of these beta-blockers is lost if too great a dose is administered. The dose-to-effect modality of administration of these beta-blockers described in the following examples enables the physician, other medical professional, or even the patient, in some cases, to administer a proper dose of these beta-blockers.

All beta-blockers, however, if administered in excess may result in impaired pulmonary function, wheezing, and asthmatic attacks. In addition, serious adverse cardiovascular effects such as bradycardia, profound hypotension, and even precipitation of severe congestive heart failure may result from the excess use of beta-blockers. Adverse central nervous system effects of overdose of beta-blockers include dizziness, fatigue, mental depression, and in some cases hallucinations; short-term memory impairment and vertigo have also been observed. There may also be adverse gastrointestinal reactions, such as diarrhea and nausea.

The following examples demonstrate that beta-blockers can be safely administered in a dose-to-effect manner thereby avoiding the harmful and undesirable side effects of overdosing and underdosing. Safe administration of beta-blockers is accomplished by the dose-to-effect modality of administration described in the following examples wherein a precise dose of beta-blockers is administered to the patient.

Although the following examples only demonstrate the methods and compositions of the present invention as they relate to specific drugs having a beta-blocking effect in the patient, it will be appreciated that other drugs may also be utilized within the scope of the present invention. What is important is that the drug be lipophilic, potent, and fast-acting so that the desired beta-blocking effects can be observed by the medical professional (or the patient himself if the drug is self-administered) in sufficient time to remove the lollipop from the patient's mouth in time to prevent overdosing. Indeed, any beta-blocker having the characteristics described above may be administered to a patient according to the present invention.

EXAMPLE 12

A drug-containing lollipop in accordance with the present invention is prepared substantially according to the procedure of Example 2, except that the drug esmolol in a lollipop dose of 5 milligrams is substituted for the nifedipine. The esmolol-containing lollipop is used in the procedure set forth in Example 3 for treating a patient with hypertension. As the patient sucks on the lollipop, the patient's blood pressure is rapidly lowered to a predetermined value.

EXAMPLE 13

A drug-containing lollipop in accordance with the present invention is prepared substantially according to the procedure of Example 2, except that the drug esmolol in a lollipop dose of 6 milligrams is substituted for the nifedipine. The esmolol-containing lollipop is used in the procedure set forth in Example 4 for rapid relief from angina. The patient experiences some relief within 3 minutes, and after about 5 minutes the anginal pain is substantially relieved.

EXAMPLE 14

A drug-containing lollipop in accordance with the present invention is prepared substantially according to the procedure of Example 2, except that the drug nadolol in a lollipop dose of 40 milligrams is substituted for the nifedipine. The nadolol-containing lollipop is used in the procedure set forth in Example 3 for treating a patient with hypertension. As the patient sucks on the lollipop, the patient's blood pressure is rapidly lowered to a predetermined value.

EXAMPLE 15

A drug-containing lollipop in accordance with the present invention is prepared substantially according to the procedure of Example 2, except that the drug nadolol in a lollipop dose of 80 milligrams is substituted for the nifedipine. The nadolol-containing lollipop is used in the procedure set forth in Example 4 for rapid relief from angina. The patient experiences some relief within 5 minutes, and after about 8 minutes the anginal pain is substantially relieved.

EXAMPLE 16

A drug-containing lollipop in accordance with the present invention is prepared substantially according to the procedure of Example 2, except that the drug propranolol in a lollipop dose of 10 milligrams is substituted for the nifedipine. The propranolol-containing lollipop is used in the procedure set forth in Example 3 for treating a patient with hypertension. As the patient sucks on the lollipop, the patient's blood pressure is rapidly lowered to a predetermined value.

EXAMPLE 17

A drug-containing lollipop in accordance with the present invention is prepared substantially according to the procedure of Example 2, except that the drug propranolol in a lollipop dose of 10 milligrams is substituted for the nifedipine. The propranolol-containing lollipop is used in the procedure set forth in Example 4 for rapid relief from angina. The patient experiences some relief within 2 minutes, and after about 8 minutes the anginal pain is substantially relieved.

EXAMPLE 18

A drug-containing lollipop in accordance with the present invention is prepared substantially according to the procedure of Example 2, except that the drug pindolol in a lollipop dose of 5 milligrams is substituted for the nifedipine. The pindolol-containing lollipop is used in the procedure set forth in Example 3 for treating a patient with hypertension. As the patient sucks on the lollipop, the patient's blood pressure is rapidly lowered to a predetermined value.

EXAMPLE 19

A drug-containing lollipop in accordance with the present invention is prepared substantially according to the procedure of Example 2, except that the drug pindolol in a lollipop dose of 6 milligrams is substituted for the nifedipine. The pindolol-containing lollipop is used in the procedure set forth in Example 4 for rapid relief from angina. The patient experiences some relief within 3 minutes, and after about 5 minutes the anginal pain is substantially relieved.

EXAMPLE 20

A drug-containing lollipop in accordance with the present invention is prepared substantially according to the procedure of Example 1. In this example, timolol in a lollipop dose of 10 milligrams is used. The timolol-containing, candy matrix lollipop is used in the procedure set forth in Example 5 for treating a patient with hypertension. As the patient sucks on the lollipop, the patient's blood pressure is rapidly lowered to a predetermined value.

EXAMPLE 21

A drug-containing lollipop in accordance with the present invention is prepared substantially according to the procedure of Example 1. In this example, timolol in a lollipop dose of 15 milligrams is used. The timolol-containing, candy matrix lollipop is used in the procedure set forth in Example 6 for rapid relief from angina. The patient experiences some relief within 3 minutes, and after about 5 minutes the anginal pain is substantially relieved.

EXAMPLE 22

A drug-containing lollipop in accordance with the present invention is prepared substantially according to the procedure of Example 2, except that the drug timolol in a lollipop dose of 20 milligrams is substituted for the nifedipine. The timolol-containing lollipop is used in the procedure set forth in Example 3 for treating a patient with hypertension. As the patient sucks on the lollipop, the patient's blood pressure is rapidly lowered to a predetermined value.

EXAMPLE 23

A drug-containing lollipop in accordance with the present invention is prepared substantially according to,the procedure of Example 2, except that the drug timolol in a lollipop dose of 25 milligrams is substituted for the nifedipine. The timolol-containing lollipop is used in the procedure set forth in Example 4 for rapid relief from angina. The patient experiences some relief within 3 minutes, and after about 4 minutes the anginal pain is substantially relieved.

EXAMPLE 24

A drug-containing lollipop in accordance with the present invention is prepared substantially according to the procedure of Example 2, except that the drug atenolol in a lollipop dose of 50 milligrams is substituted for the nifedipine. The atenolol-containing lollipop is used in the procedure set forth in Example 3 for treating a patient with hypertension. As the patient sucks on the lollipop, the patient's blood pressure is rapidly lowered to a predetermined value.

EXAMPLE 25

A drug-containing lollipop in accordance with the present invention is prepared substantially according to the procedure of Example 2, except that the drug atenolol in a lollipop dose of 80 milligrams is substituted for the nifedipine. The atenolol-containing lollipop is used in the procedure set forth in Example 4 for rapid relief from angina. The patient experiences some relief within 1 minute, and after about 3 minutes the anginal pain is substantially relieved.

EXAMPLE 26

A drug-containing lollipop in accordance with the present invention is prepared substantially according to the procedure of Example 1, except that the drug metoprolol in a lollipop dose of 25 milligrams is substituted for the timolol. The metoprolol-containing lollipop is used in the procedure set forth in Example 3 for treating a patient with hypertension. As the patient sucks on the lollipop, the patient's blood pressure is rapidly lowered to a predetermined value.

EXAMPLE 27

A drug-containing lollipop in accordance with the present invention is prepared substantially according to the procedure of Example 2, except that the drug metoprolol in a lollipop dose of 40 milligrams is substituted for the nifedipine. The metoprolol-containing lollipop is used in the procedure set forth in Example 4 for rapid relief from angina. The patient experiences some relief within 3 minutes, and after about 4.5 minutes the anginal pain is substantially relieved.

Vasodilating drugs which may be administered according to the methods and compositions of the present invention include the organic nitrates, such as isosorbide and nitroglycerin.

Organic nitrates relax vascular smooth muscles. They are particularly useful for relief of angina pectoris, for prophylactic management of situations likely to provoke angina attacks, and for long-term prophylactic management of angina pectoris. However, an overdose of isosorbide may result in headache, dizziness, nausea, tachycardia, hypotension, fainting, or other dangerous depressions of vital body functions.

Thus, it will be appreciated that overdosing the patient with any of these vasodilating drugs may result in serious side effects to the patient which may cause the patient great discomfort and, in some instances, may be so serious as to cause dangerous depression of vital organs.

The following examples demonstrate methods and compositions for safely administering such vasodilating drugs in a dose-to-effect manner such that overdosing is avoided thereby avoiding the undesirable and dangerous side effects which may result from overdosing of these vasodilating drugs.

Although the following examples only demonstrate the methods and compositions of the present invention as they relate to specific vasodilating drugs, it will be appreciated that other drugs may also be utilized within the scope of the present invention. What is important is that the drug be lipophilic, potent, and fast-acting so that the desired effects can be observed by the medical professional (or the patient himself if the drug is self-administered) in sufficient time to remove the lollipop from the patient's mouth in time to prevent overdosing. Indeed, any vasodilating drug having the characteristics described above may be administered to a patient according to the present invention.

EXAMPLE 28

A drug-containing lollipop in accordance with the present invention is prepared substantially according to the procedure of Example 2, except that the drug isosorbide in a lollipop dose of 2.5 milligrams is substituted for the nifedipine. The isosorbide-containing lollipop is used in the procedure set forth in Example 3 for treating a patient with hypertension. As the patient sucks on the lollipop, the patient's blood pressure is rapidly lowered to a predetermined value.

EXAMPLE 29

A drug-containing lollipop in accordance with the present invention is prepared substantially according to the procedure of Example 2, except that the drug isosorbide in a lollipop dose of 20 milligrams is substituted for the nifedipine. The isosorbide-containing lollipop is used in the procedure set forth in Example 4 for rapid relief from angina. The patient experiences some relief within 1.5 minutes, and after about 3 minutes the anginal pain is substantially relieved.

EXAMPLE 30

In the procedure of this example, a patient is given an isosorbide-containing lollipop as treatment for congestive heart failure. In this example, the isosorbide-containing lollipop was prepared substantially according to the procedure of Example 2, except that the drug isosorbide in a lollipop dose of 25 milligrams is substituted for nifedipine. Shortly after initiating the administration of the isosorbide-containing lollipop, the patient's breathing rate decreases, and the patient no longer experiences a shortness of breath. The patient's exercise tolerances increase, and the heart rate of the patient decreases. In addition, there is "ST wave" improvement in EKG. As the blood pressure decreases, the "ST segment" of the EKG approaches normal.

The following examples describe the preparation and, use of a drug-containing lollipop wherein the drug dispersed within the lollipop is a hypotensive drug which reduces blood pressure by lowering the total peripheral resistance by direct vasodilation. Hypotensive drugs of this nature, such as nitroprusside and hydralazine, are particularly potent and are usually given in an emergency or when other hypotensive treatments have failed. Slight overdoses of this type of hypotensive drug may result in headache, tachycardia, nausea, and diarrhea, and may even precipitate angina pectoris or ventricular arrhythmia.

Still other hypotensive drugs, such as prazosin, are $alpha_1$-blockers which are also capable of reducing blood pressure by lowering the total peripheral resistance as a result of vasodilating effects. An overdose of prazosin may result in headache, drowsiness, palpitation, nausea, and even fainting.

Labetolol is a unique hypotensive drug which combines the features of alpha-blockers with beta-blockers. Blood pressure is reduced due to a decrease in systemic vascular resistance, but usually without a substantial reduction or increase in heart rate, cardiac output, or stroke volume. Unfortunately, labetolol shares the toxic potentials of both the beta and the alpha-blocking agents. In particular, labetolol overdose may promote or exacerbate congestive heart failure, bronchospasm, hypotension, and bradycardia.

Other hypotensive drugs, such as methyldopa and clonidine, inhibit sympathetic vasomotor centers thereby reducing peripheral central nervous system activity, blood pressure, and heart rate with little change in total peripheral resistance. An overdose of these drugs may result in drowsiness, headache, nausea, dry mouth, palpitation and tachycardia, bradycardia, congestive heart failure, rash, impotence, hepatic abnormalities, and muscle cramps.

Thus, it will be appreciated that overdosing the patient with any of these hypotensive drugs may result in serious side effects to the patient which may cause the patient great discomfort and, in some instances, may be so serious as to cause failure of vital organs resulting in death.

The following examples demonstrate methods and compositions for safely administering such hypotensive drugs in a dose-to-effect manner such that the undesirable and dangerous side effects which may result from overdosing of these hypotensive drugs are avoided.

Although the following examples only demonstrate the methods and compositions of the present invention as they relate to specific hypotensive drugs, it will be appreciated that other drugs may also be utilized within the scope of the present invention. What is important is that the drug be lipophilic, potent, and fast-acting so that the desired effects can be observed by the medical professional (or the patient himself if the drug is self-administered) in sufficient time to remove the lollipop from the patient's mouth in time to prevent overdosing. Indeed, any hypotensive drug having the characteristics described above may be administered to a patient according to the present invention.

EXAMPLE 31

A drug-containing lollipop in accordance with the present invention is prepared substantially according to the procedure of Example 2, except that the drug clonidine in a lollipop dose of 0.1 milligrams is substituted for the nifedipine. The clonidine-containing lollipop is used in the procedure set forth in Example 3 for treating a patient with hypertension. As the patient sucks on the lollipop, the patient's blood pressure is rapidly lowered to a predetermined value.

EXAMPLE 32

In the procedure of this example, a patient is given a clonidine-containing lollipop as treatment for hypertension. In this example, the clonidine-containing lollipop was prepared substantially according to the procedure of Example 2, except that the drug clonidine in a lollipop dose of 0.2 milligrams is substituted for nifedipine. Substantially the same effects as those set forth in Example 40 are observed.

EXAMPLE 33

A drug-containing lollipop in accordance with the present invention is prepared substantially according to the procedure of Example 2, except that the drug hydralizine in a lollipop dose of 10 milligrams is substituted for the nifedipine. The hydralizine-containing lollipop is used in the procedure set forth in Example 3 for treating a patient with hypertension. As the patient sucks on the lollipop, the patient's blood pressure is rapidly lowered to a predetermined value.

EXAMPLE 34

In the procedure of this example, a patient is given a hydralizine-containing lollipop as treatment for hypertension. In this example, the hydralizine-containing lollipop was prepared substantially according to the procedure of Example 2, except that the drug hydralizine in a lollipop dose of 20 milligrams is substituted for nifedipine. Substantially the same effects as those set forth in Example 40 are observed.

EXAMPLE 35

In the procedure of this example, a patient is given a nitroprusside-containing lollipop as treatment for hypertension. In this example, the nitroprusside-containing lollipop was prepared substantially according to the procedure of Example 2, except that the drug nitroprusside in a lollipop dose of 10 milligrams is substituted for nifedipine. The patient's blood pressure decreases by about 20 mm Hg after one minute, and by 10mm Hg more, at which time the lollipop is removed.

EXAMPLE 36

A drug-containing lollipop in accordance with the present invention is prepared substantially according to the procedure of Example 2, except that the drug methyldopa in a lollipop dose of 250 milligrams is substituted for the nifedipine. The methyldopa-containing lollipop is used in the procedure set forth in Example 3 for treating a patient with hypertension. As the patient sucks on the lollipop, the patient's blood pressure is rapidly lowered to a predetermined value.

EXAMPLE 37

In the procedure of this example, a patient is given a methyldopa-containing lollipop as treatment for hypertension. In this example, the methyldopa-containing lollipop was prepared substantially according to the procedure of Example 2, except that the drug methyldopa in a lollipop dose of 400 milligrams is substituted for nifedipine. Substantially the same effects as those set forth in Example 40 are observed.

EXAMPLE 38

In the procedure of this example, a patient is given a methyldopa-containing lollipop as treatment for hypertension. In this example, the methyldopa-containing lollipop was prepared substantially according to the procedure of Example 1, except that the drug methyldopa in a lollipop dose of 400 milligrams is substituted for timolol. As the patient sucks on the candy matrix lollipop, substantially the same effects as those set forth in Example 40 are observed.

EXAMPLE 39

A drug-containing lollipop in accordance with the present invention is prepared substantially according to the procedure of Example 2, except that the drug prazosin in a lollipop dose of 3 milligrams is substituted for the nifedipine. The prazosin-containing lollipop is used in the procedure set forth in Example 3 for treating a patient with hypertension. As the patient sucks on the lollipop, the patient's blood pressure is rapidly lowered to a predetermined value.

EXAMPLE 40

In the procedure of this example, a patient is given a prazosin-containing lollipop as treatment for hypertension. In this example, the prazosin-containing lollipop was prepared substantially according to the procedure of Example 2, except that the drug prazosin in a lollipop dose of 4 milligrams is substituted for nifedipine. The patient's blood pressure decreases by about 20 mm Hg after one minute, and by 10 mm Hg more, at which time the lollipop is removed.

EXAMPLE 41

In the procedure of this example, a patient is given a prazosin-containing lollipop as treatment for hypertension. In this example, the prazosin-containing lollipop was prepared substantially according to the procedure of Example 1, except that the drug prazosin in a lollipop dose of 4 milligrams is substituted for timolol. As the patient sucks on the candy matrix lollipop, substantially the same effects as those set forth in Example 40 are observed.

EXAMPLE 42

A drug-containing lollipop in accordance with the present invention is prepared substantially according to,the procedure of Example 2, except that the drug labetolol in a lollipop dose of 100 milligrams is substituted for the nifedipine. The labetolol-containing lollipop is used in the procedure set forth in Example 3 for treating a patient with hypertension. As the patient sucks on the lollipop, the patient's blood pressure is rapidly lowered to a predetermined value.

EXAMPLE 43

In the procedure of this example, a patient is given a labetolol-containing lollipop as treatment for hypertension. In this example, the labetolol-containing lollipop was prepared substantially according to the procedure of Example 2, except that the drug labetolol in a lollipop dose of 200 milligrams is substituted for nifedipine. Substantially the same effects as those set forth in Example 40 are observed.

The following examples describe the preparation and use of a drug-containing lollipop wherein the drug dispersed within the lollipop is a hypotensive drug which reduces blood pressure by suppressing the renin-angio-tensin-aldosterone system. These drugs inhibit the angiotensin-converting enzyme thereby resulting in arterial and possibly venous dilation. Thus, blood pressure is reduced by decreasing the total peripheral resistance with no change or an increase in heart rate, stroke volume, or cardiac output.

These ACE-inhibiting drugs, if administered in excess, may also result in neutro-penia, an abnormally low white blood cell count, which may further lead to systemic or regional infections and possible death. Other adverse effects from overdosing of ACE inhibitors include proteinuria, rash, taste impairment, excessive hypotension, tachycardia, angina, palpitations, and even myocardial infarction and congestive heart failure.

Thus, it will be appreciated that overdosing the patient with any of these hypotensive drugs may result in serious side effects to the patient which may cause the patient great discomfort and, in some instances, may be so serious as to cause loss of vital organs resulting in death.

The following examples demonstrate methods and compositions for safely administering such hypotensive drugs in a dose-to-effect manner such that overdosing is avoided thereby avoiding the undesirable and dangerous side effects which may result from overdosing.

Although the following examples only demonstrate the methods and compositions of the present invention as they relate to specific hypotensive drugs, it will be appreciated that other drugs may also be utilized within the scope of the present invention. What is important is that the drug be lipophilic, potent, and fast-acting so that the desired effects can be observed by the medical professional (or the patient himself if the drug is self-administered) in sufficient time to remove the lollipop from the patient's mouth in time to prevent overdosing. Indeed, any hypotensive drug having the characteristics described above may be administered to a patient according to the present invention.

EXAMPLE 44

A drug-containing lollipop in accordance with the present invention is prepared substantially according to the procedure of Example 2, except that the drug captopril in a lollipop dose of 25 milligrams is substituted for the nifedipine. The captopril-containing lollipop is used in the procedure set forth in Example 3 for treating a patient with hypertension. As the patient sucks on the lollipop, the patient's blood pressure is rapidly lowered to a predetermined value.

EXAMPLE 45

In the procedure of this example, a patient is given a captopril-containing lollipop as treatment for hypertension. In this example, the captopril-containing lollipop was prepared substantially according to the procedure of Example 2, except that the drug captopril in a lollipop .dose of 70 milligrams is substituted for nifedipine. Substantially the same effects as those set forth in Example 40 are observed.

EXAMPLE 46

A drug-containing lollipop in accordance with the present invention is prepared substantially according to the procedure of Example 2, except that the drug enalapril in a lollipop dose of 5 milligrams is substituted for the nifedipine. The enalapril-containing lollipop is used in the procedure set forth in Example 3 for treating a patient with hypertension. As the patient sucks on the lollipop, the patient's blood pressure is rapidly lowered to a predetermined value.

EXAMPLE 47

In the procedure of this example, a patient is given an enalapril-containing lollipop as treatment for hypertension. In this example, the enalapril-containing lollipop was prepared substantially according to the procedure of Example 2, except that the drug enalapril in a lollipop dose of 10 milligrams is substituted for nifedipine. Substantially the same effects as those set forth in Example 40 are observed.

The physician also has at his disposal a number of cardiac drugs useful for treating ventricular fibrillation, acute ventricular arrhythmias, and congestive heart failure. Again, these drugs, while useful, can be very dangerous when the patient's susceptability to the drug makes it difficult to know the proper dose.

Amrinone, for example, is an inotropic drug which increases the force and velocity of myocardial systolic contraction. In addition, amrinone has vasodilatory activity affecting vascular smooth muscle. In patients with congestive heart failure, amrinone produces substantial increases in cardiac output.

However, serious adverse effects may arise in the event of an overdose of amrinone; these adverse effects include: thrombocytopenia, arrhythmias, hypotension, nausea, vomiting, diarrhea, hepatotixicity marked by abnormal liver function, and hypersensitivity.

Thus, it will be appreciated that overdosing the patient with these cardiac drugs may result in serious side effects to the patient which may cause the patient great discomfort.

The following example demonstrates methods and compositions for safely administering such cardiac drugs in a dose-to-effect manner such that overdosing is avoided thereby avoiding the undesirable and dangerous side effects which may result from overdosing of these cardiac drugs.

Although the following example only demonstrates the methods and compositions of the present invention as it relates to amrinone, it will be appreciated that other drugs may also be utilized within the scope of the present invention. What is important is that the drug be lipophilic, potent, and fast-acting so that the desired effects can be observed by the medical professional (or the patient himself if the drug is self-administered) in sufficient time to remove the lollipop from the patient's mouth in time to prevent overdosing. Indeed, any cardiac drug having the characteristics described above may be administered to a patient according to the present invention.

EXAMPLE 48

A drug-containing lollipop in accordance with the present invention is prepared substantially according to the procedure of Example 2, except that the drug amrinone in a lollipop dose of 50 milligrams is substituted for the timolol. The amrinone-containing lollipop is used in the procedure set forth in Example 30 for treating a patient with congestive heart failure. As the patient sucks on the lollipop, substantially the same effects as those set forth with respect to Example 41 are observed.

Anti-arrhythmic drugs, such as bretylium and lidocaine, may also be safely administered to a patient according to the methods and compositions of the present invention as is demonstrated in the following examples.

Bretylium and lidocaine are well-known anti-arrhythmic drugs. Bretylium is used in the prophylaxis and treatment of ventricular fibrillation. However, because it commonly causes hypotension, and may increase ventricular irritability, bretylium must be used with care. Lidocaine is a CNS-depressing drug which controls ventricular arrhythmias. It also produces sedative, analgesic, and anti-convulsant effects. Overdoses may result in seizures, respiratory arrest, dizziness, nausea, unconsciousness, or even coma.

Thus, it will be appreciated that overdosing the patient with any anti-arrhythmic drugs may result in undesirable side effects to the patient which may cause the patient great discomfort.

The following examples demonstrate methods and compositions for safely administering such anti-arrhythmic drugs in a dose-to-effect manner such that overdosing is avoided thereby avoiding the undesirable and dangerous side effects which may result from overdosing of these anti-arrihythmic drugs.

Although the following examples only demonstrate the methods and compositions of the present invention as they relate to specific anti-arrhythmic drugs, it will be appreciated that other drugs may also be utilized within the scope of the present invention. What is important is that the drug be lipophilic, potent, and fast-acting so that the desired effects can be observed by the medical professional (or the patient himself if the drug is self-administered) in sufficient time to remove the lollipop from the patient's mouth in time to prevent overdosing. Indeed, any antiarrhythmic drug having the characteristics described above may be administered to a patient according to the present invention.

EXAMPLE 49

In the procedure of this example, a patient experiencing ventricular fibrillation is given a bretylium-containing lollipop. In this example, the lollipop is prepared substantially according to the procedure of Example 2 except that the drug bretylium in a lollipop dose of 60 milligrams is substituted for nifedipine. Rapid conversion to normal sinus rhythm is observed. The bretylium-containing lollipop is removed and discarded.

EXAMPLE 50

In the procedure of this example, a patient experiencing acute ventricular arrhythmias is given a lidocaine-containing lollipop. In this example, the lollipop is prepared substantially according to the procedure of Example 2 except that the drug lidocaine in a lollipop dose of 10 milligrams is substituted for nifedipine. Rapid conversion to normal sinus rhythm is observed. The lidocaine-containing lollipop is removed and discarded.

EXAMPLES 51–55

In the procedures of these examples, drug-containing lollipops in accordance with the present invention are prepared according to the procedures of Example 1, except that the following drugs are dispersed in the "candy" matrix in the indicated doses and are substituted for the timolol.

TABLE II

| Example | Drug | Dose |
|---------|------|------|
| 51 | Diltiazem | 30 milligrams |
| 52 | Pindolol | 5 milligrams |
| 53 | Metoprolol | 25 milligrams |
| 54 | Prazosin | 3 milligrams |
| 55 | Methyldopa | 250 milligrams |

EXAMPLES 56–58

In the procedures of these examples, drug-containing lollipops in accordance with the present invention are prepared according to the procedures of Example 1, except that the following drugs are dispersed in the "candy" matrix in the indicated doses and are substituted for the timolol.

TABLE III

| Example | Drug | Dose |
|---------|------|------|
| 56 | Diltiazem | 50 milligrams |
| 57 | Pindolol | 6 milligrams |
| 58 | Metoprolol | 40 milligrams |

These drug-containing lollipops are used in the procedure set forth in Example 4 in order to relieve immediate anginal pain. As the patient sucks on the candy matrix lollipop, the patient's experiences relief from anginal pain at substantially the same rates as the respective compressed-powder, drug-containing lollipops of Examples 8, 21, and 27.

In addition to drugs for treating cardiovascular conditions, many new drugs for treatment of renal vascular functions have been developed in recent years. Like most drugs affecting the cardiovascular system, the drugs affecting the renal vascular system must be precisely administered to avoid serious side effects or the dangers of overdosing and underdosing.

One of the most useful drugs employed today for increasing renal blood flow and urine output is dopamine. In its clinical application, dopamine is administered until urine output is significantly increased or approaches a normal stage. Despite its benefits, the detriment of using too much dopamine is reflected in increases in the heart rate, blood pressure, cardiac output, and myocardial oxygen consumption. These effects are extremely dangerous in patients with ischemic cardiac disease. Hence, precise dosage control is critical to the effective use of dopamine.

Thus, it will be appreciated that overdosing the patient with any of these renal vascular-acting drugs may result in serious side effects to the patient which may cause the patient great discomfort and, in some instances, may be so serious as to cause failure of vital organs resulting in death.

The following examples demonstrate methods and compositions for safely administering such renal vascular-acting drugs in a dose-to-effect manner such that overdosing is avoided thereby avoiding the undesirable and dangerous side effects which may result from overdosing.

Although the following examples only demonstrate the methods and compositions of the present invention as they relate to dopamine, it will be appreciated that other drugs may also be utilized within the scope of the present invention. What is important is that the drug be lipophilic, potent, and fast-acting so that the desired effects can be observed by the medical professional (or the patient himself if the drug is self-administered) in sufficient time to remove the lollipop from the patient's mouth in time to prevent overdosing. Indeed, any renal vascular-acting drug having the characteristics described above may be administered to a patient according to the present invention.

EXAMPLE 59

In the procedure of this example, a patient who is presently experiencing oliguria is given a dopamine-containing lollipop in order to immediately increase the patient's urine output. The lollipop of this example is made according to the procedures of Example 2, except that dopamine in a lollipop dose of 350 milligrams is used instead of nifedipine.

After the patient is permitted to suck on the lollipop for only a matter of a few minutes, the urine output is increased with no change in the heart rate of blood pressure.

EXAMPLE 60

In the procedure of this example, a patient who is presently experiencing insufficient urine output is given a dopamine-containing lollipop according to the procedures of Example 59, except that the dopamine is in a lollipop dose of 700 milligrams.

After the patient is permitted to suck on the lollipop for only a few minutes, the urine output is increased with no change in the heart rate or blood pressure.

From the foregoing, it will be appreciated that the present invention allows great flexibility and permits physician control on a case-by-case basis with respect to the dose given to a particular patient and the rate at which that dose is given.

The use of a drug-containing lollipop for administration of cardiovascular-acting and renal vascular-acting agents provides for much faster onset than oral administration and also avoids unacceptable loss of drug on a first pass through the liver before systemic distribution. Further, the use of a lollipop in accordance with the present invention provides for a relatively level drug plasma concentration, which is preferable when dealing with cardiovascular and renal vascular related drugs.

Further, a physician can easily monitor a patient's condition to ensure the patient receives a dose adequate to evoke a desired cardiovascular state. If necessary, the physician can instruct the patient to alter the aggressiveness with which he sucks the lollipop, or the physician can take the lollipop from the patient.

A patient can also self-administer suitable anti-anginal medication using a lollipop in accordance with the present invention. Thus, a patient can place a drug-containing lollipop passively in his mouth for continuous low level administration of a drug, or the patient can take a lick of the lollipop from time to time as it may be needed to reduce his own subjective experience of the symptoms of the cardiovascular or renal vascular condition.

Although the methods and compositions of the present invention have been described with reference to specific examples, it is to be understood that the methods and compositions of the present invention may be practiced in other forms without parting from its spirit or essential characteristics. The described methods and compositions are considered in all respects only as illustrative, and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A composition for use in inducing a predetermined systemic modification of cardiovascular functions in a patient, said composition comprising:

lipophilic drug means for inducing a predetermined systemic modification of cardiovascular functions in the patient that can be observed before overdosage in the patient occurs;

carbohydrate releasing means, the releasing means uniformly incorporating said drug means, for simultaneously releasing said drug means over a period of time as the releasing means is dissolved while being sucked and held passively in the mouth of the patient for substantially complete administration via absorption through mucosal tissues of the mouth, pharynx, and esophagus in a dose-to-effect manner such that systemic modification of cardiovascular functions is achieved and maintained; and a stick secured to the releasing means, for permitting convenient insertion of the releasing means into the mouth of the patient, and for quantitatively and conveniently permitting insertion and removal of the releasing means in response to the observed effect of the drug means on the patient in order to maintain a desired effect over a prolonged period of time in response to susceptibility and needs of an individual patient, the stick remaining after the releasing means has completely dissolved.

2. A composition as defined in claim 1, wherein the stick means is a stick with an enlarged end to prevent the stick from getting caught in the patient's mouth.

3. A composition as defined in claim 1, wherein the drug means comprises an antiarrhythmic drug.

4. A composition as defined in claim 1, wherein the drug means comprises a hypotensive drug.

5. A composition as defined in claim 1, wherein the drug means comprises a vasodilating drug.

6. A composition as defined in claim 1, wherein the drug means comprises an anti-anginal drug.

7. A composition as defined in claim 1, wherein the drug means comprises an inotropic drug.

8. A composition as defined in claim 5, wherein the vasodilating drug is a calcium channel blocking agent.

9. A composition as defined in claim 5, wherein the vasodilating drug is an organic nitrate.

10. A composition as defined in claim 4, wherein the hypotensive drug is a beta-adrenergic blocking agent.

11. A composition as defined in claim 1, wherein the releasing means comprises an inner carbohydrate matrix containing the drag means in a suitable concentration for maintaining the desired cardiovascular, vasodilating, anti-hypertensive, or anti-anginal effect, and an outer carbohydrate matrix covering the inner matrix, said outer matrix containing the drug means in a suitable concentration for inducing the desired cardiovascular, vasodilating, anti-hypertensive, or anti-anginal effect.

12. A composition as defined in claim 1, wherein the releasing means comprises a mixture of maltodextrin and compressible sugar in a ratio in the range of from about 1:1 to about 1:4.

13. A composition as defined in claim 11, wherein the releasing means comprises a flavoring in order to mask the flavor of the drug.

14. A composition as defined in claim 1, wherein the releasing means includes a hydrophobic material such that the releasing means becomes less soluble when placed in the patient's mouth.

15. A composition as defined in claim 1, wherein the releasing means includes a coloring agent.

16. A composition as defined in claim 1, wherein the stick means is secured to the releasing means by compressing the releasing means around a portion of the stick means such that the releasing means remains cohesively secured to the stick means.

17. A composition as defined in claim 1, wherein the drug means is lipophilic.

18. A composition as defined in claim 1, wherein the drug means is potent and fast-acting.

19. A composition as defined in claim 1, wherein the releasing means comprises a soluble matrix material, the drug means being dispersed substantially uniformly within the matrix.

20. A composition as defined in claim 1, wherein the ratio of the drug means to the releasing means may be varied in order to vary the rate of uptake of the drug means by the body.

21. A composition for use in inducing a predetermined systemic modification of cardiovascular functions in a patient, said composition comprising:

a pharmaceutically effective dose of a lipophilic drug absorbable through mucosal tissues of the mouth, pharynx, and esophagus, for inducing a predetermined systemic modification of cardiovascular functions in the patient such that effects of the pharmaceutically effective dose can be observed before overdosage in the patient occurs;

a soluble carbohydrate matrix material, substantially uniformly incorporating the pharmaceutically effective dose allowing both the matrix material and the drug dosage to be simultaneously dissolved, to release said pharmaceutically effective dose over a period of time, for absorption through mucosal tissues of the mouth, pharynx, and esophagus, wherein the matrix comprises an outer matrix containing the drug in a suitable concentration for inducing the desired cardiovascular effect, and an inner matrix containing the drug in a suitable concentration for maintaining the desired cardiovascular effect; and means, secured to the soluble matrix material, for quantitatively and conveniently permitting insertion of the soluble matrix material drug-containing matrix into the mouth of a patient, and for quantitatively and conveniently permitting insertion and removal thereof, in response to the effect of the pharmaceutically effective dose on the patient in order to maintain a desired effect over a prolonged period of time in response to susceptibility and needs of an individual patient.

22. A composition for use in inducing a predetermined systemic modification of cardiovascular functions in a patient, said composition comprising:

a pharmaceutically effective dose of a lipophilic drug absorbable through mucosal tissues of the mouth, pharynx, and esophagus, for inducing a predetermined systemic modification of cardiovascular functions in the patient, such that effects of the pharmaceutically effective dose can be observed before overdosage in the patient occurs;

a soluble carbohydrate matrix material substantially uniformly incorporating said pharmaceutically effective dose, for releasing said pharmaceutically effective dose over a period of time, for absorption through mucosal tissues of the mouth, pharynx, and esophagus, wherein the matrix comprises an outer matrix containing the drug in a suitable concentration for rapidly inducing a desired vasodilating effect, and an inner matrix containing the drug in a suitable concentration for maintaining the desired vasodilating effect; and means, secured to the soluble matrix material, for quantitatively and conveniently permitting insertion of the soluble matrix material into the mouth of a patient, and for quantitatively and conveniently permitting insertion and removal thereof, in response to the effect of the pharmaceutically effective dose on the patient on order to maintain a desired effect over a prolonged period of time in response to susceptibility and needs of an individual patient.

23. A composition for use in inducing a predetermined systemic modification of cardiovascular functions in a patient, said composition comprising:

a pharmaceutically effective dose of a lipophilic drug absorbable through mucosal tissues of the mouth, pharynx, and esophagus, for inducing a predetermined systemic modification of cardiovascular functions in the patient, such that effects of the pharmaceutically effective dose can be observed before overdosage in the patient occurs;

a soluble carbohydrate matrix material substantially uniformly incorporating said pharmaceutically effective dose, for releasing said pharmaceutically effective dose over a period of time, for absorption through mucosal tissues of the mouth, pharynx, and esophagus, wherein the matrix comprises an outer matrix containing the drug in a suitable concentration for inducing a desired anti-hypertensive effect, and an inner matrix containing the drug in a suitable concentration for maintaining the desired anti-hypertensive effect; and means, secured to the soluble matrix material, for quantitatively and conveniently permitting insertion of the soluble matrix material into the mouth of a patient, and for quantitatively and conveniently permitting insertion and removal thereof, in response to the effect of the pharmaceutically effective dose on the patient on order to maintain a desired effect over a prolonged period of time in response to susceptibility and needs of an individual patient.

24. A composition for use in inducing a predetermined systemic modification of cardiovascular functions in a patient, said composition comprising:

a pharmaceutically effective dose of a lipophilic drug absorbable through mucosal tissues of the mouth, pharynx, and esophagus, for inducing a predetermined systemic modification of cardiovascular functions in the patient, such that effects of the pharmaceutically effective dose can be observed before overdosage in the patient occurs;

a soluble carbohydrate matrix material substantially uniformly incorporating said pharmaceutically effective dose, for releasing said pharmaceutically effective dose over a period of time, for absorption through mucosal tissues of the mouth, pharynx, and esophagus, wherein the matrix comprises an outer matrix containing the drug in a suitable concentration for inducing a desired anti-anginal effect, and an inner matrix containing the drug in a suitable concentration for inducing a desired anti-anginal effect, and an inner matrix containing the drug in a suitable concentration for maintaining the desired anti-anginal effect; and means, secured to the soluble matrix material, for quantitatively and conveniently permitting insertion of the soluble matrix material into the mouth of a patient, and for quantitatively and conveniently permitting insertion and removal thereof, in response to the effect of the pharmaceutically effective dose on the patient on order to maintain a desired effect over a prolonged period of time in response to susceptibility and needs of an individual patient.

25. A composition for use in inducing a predetermined systemic modification of cardiovascular functions in a patient, said composition comprising;

a pharmaceutically effective dose of a lipophilic drug absorbable through mucosal tissues of the mouth, pharynx, and esophagus, for inducing a predetermined systemic modification of cardiovascular functions in the patient, such that effects of the pharmaceutically effective dose can be observed before overdosage in the patient occurs;

a soluble carbohydrate matrix material substantially uniformly incorporating said pharmaceutically effective dose, for releasing said pharmaceutically effective dose over a period of time, for absorption through mucosal tissues of the mouth, pharynx, and esophagus, wherein the matrix comprises an outer matrix containing the drug in a suitable concentration for inducing a desired calcium channel blocking effect, and an inner matrix containing the drug in a suitable concentration for maintaining the desired calcium channel blocking effect; and means, secured to the soluble matrix material, for quantitatively and conveniently permitting insertion of the soluble matrix material into the mouth of a patient, and for quantitatively and conveniently permitting insertion and removal thereof, in response to the effect of the pharmaceutically effective dose on the patient on order to maintain a desired effect over a prolonged period of time in response to susceptibility and needs of an individual patient.

26. A composition for use in inducing a predetermined systemic modification of cardiovascular functions in a patient, said composition comprising:

a pharmaceutically effective dose of a lipophilic drug absorbable through mucosal tissues of the mouth, pharynx, and esophagus, for inducing a predetermined systemic modification of cardiovascular functions in the patient, such that effects of the pharmaceutically effective dose can be observed before overdosage in the patient occurs;

a soluble carbohydrate matrix material substantially uniformly incorporating said pharmaceutically effective dose, for releasing said pharmaceutically effective dose over a period of time, for absorption through mucosal tissues of the mouth, pharynx, and esophagus, wherein the matrix comprises and outer matrix containing the drug in a suitable concentration for inducing a desired beta-adrenergic blocking effect, and an inner matrix containing the drug in a suitable concentration for maintaining the desired beta-adrenergic blocking effect; and means, secured to the soluble matrix material, for quantitatively and conveniently permitting insertion of the soluble matrix material into the mouth of a patient, and for quantitatively and conveniently permitting insertion and removal thereof, in response to the effect of the pharmaceutically effective dose on the patient on order to maintain a desired effect over a prolonged period of time in response to susceptibility and needs of an individual patient.

* * * * *

UNITED STATES PATENT AND TRADEMARK OFFICE
CERTIFICATE OF CORRECTION

PATENT NO. : 5,484,602
DATED : January 16, 1996
INVENTOR(S) : Theodore H. Stanley, et al.

It is certified that error appears in the above-indentified patent and that said Letters Patent is hereby corrected as shown below:

Page 2, Col. 2 of Other Publications, line 20, "1993)" should be --1983)--

Col. 2, line 18, "in," should be --in--

Col. 5, line    "a drug and" should be --a drug (and--

Col. 5, line 31, "revoke" should be --evoke--

Col. 7, line 47, "adheres," should be --adheres--

Col. 7, line 51, "mount" should be --amount--

Col. 8, line 50, "deliver drug" should be --deliver the drug--

Col. 8, line 51, "of-this" should be --of this--

Signed and Sealed this

Eleventh Day of November, 1997

Attest:

BRUCE LEHMAN

Attesting Officer

Commissioner of Patents and Trademarks